United States Patent [19]
Sperl et al.

[11] Patent Number: 6,028,116
[45] Date of Patent: Feb. 22, 2000

[54] SUBSTITUTED CONDENSATION PRODUCTS OF 1H-INDENYL-HYDROXYALKANES WITH ALDEHYDES FOR NEOPLASIA

[75] Inventors: Gerhard Sperl; Paul Gross, both of Stockton, Calif.; Klaus Brendel, Tuscon, Ariz.; Gary Piazza, Doylestown; Rifat Pamukcu, Spring House, both of Pa.

[73] Assignee: Cell Pathways, Inc., Horsham, Pa.

[21] Appl. No.: 09/054,814

[22] Filed: Apr. 3, 1998

[51] Int. Cl.$^7$ .................................................. A01N 31/00
[52] U.S. Cl. ............................................ 514/729; 514/569
[58] Field of Search ...................................... 514/729, 569

[56] References Cited

U.S. PATENT DOCUMENTS

| | | |
|---|---|---|
| 3,161,654 | 12/1964 | Shen . |
| 3,312,730 | 4/1967 | Winter et al. . |
| 3,325,358 | 6/1967 | Winter et al. . |
| 3,532,752 | 10/1970 | Shen . |
| 3,609,184 | 9/1971 | Miyai et al. . |
| 3,622,623 | 11/1971 | Shen et al. . |
| 3,631,167 | 12/1971 | Shen et al. . |
| 3,642,785 | 2/1972 | Shen et al. . |
| 3,647,858 | 3/1972 | Hinkley et al. . |
| 3,654,349 | 4/1972 | Shen et al. . |
| 3,692,651 | 9/1972 | Sletzinger . |
| 3,692,825 | 9/1972 | Conn . |
| 3,700,730 | 10/1972 | Hinkley . |
| 3,737,455 | 6/1973 | Shen et al. . |
| 3,759,987 | 9/1973 | Conn et al. . |
| 3,766,259 | 10/1973 | Sletzinger . |
| 3,772,282 | 11/1973 | Ford, Jr. . |
| 3,812,109 | 5/1974 | Shen et al. . |
| 3,812,180 | 5/1974 | Shen et al. . |
| 3,822,310 | 7/1974 | Shen et al. . |
| 3,851,063 | 11/1974 | Shen et al. . |
| 3,860,636 | 1/1975 | Shen et al. . |
| 3,868,414 | 2/1975 | Shen et al. . |
| 3,868,415 | 2/1975 | Jones . |
| 3,869,507 | 3/1975 | Jones . |
| 3,870,753 | 3/1975 | Tull et al. . |
| 3,883,660 | 5/1975 | Shen et al. ............................ 424/303 |
| 3,888,902 | 6/1975 | Shen et al. . |
| 3,897,487 | 7/1975 | Jones . |
| 3,932,498 | 1/1976 | Shen et al. . |
| 3,944,600 | 3/1976 | Tull et al. . |
| 3,954,852 | 5/1976 | Shen et al. . |
| 3,956,363 | 5/1976 | Shen et al. . |
| 3,970,693 | 7/1976 | Tull et al. . |
| 3,998,875 | 12/1976 | Tull et al. . |
| 4,207,340 | 6/1980 | Gardocki . |
| 4,233,457 | 11/1980 | Czaja et al. . |
| 4,307,114 | 12/1981 | Dvornik et al. . |
| 4,402,979 | 9/1983 | Shen et al. . |
| 4,423,074 | 12/1983 | Dvornik et al. . |
| 4,423,075 | 12/1983 | Dvornik et al. . |
| 4,656,190 | 4/1987 | Shen et al. . |
| 4,748,271 | 5/1988 | Meneghin . |
| 4,943,587 | 7/1990 | Cetenko et al. . |
| 5,093,356 | 3/1992 | Girard et al. ............................ 514/438 |
| 5,112,868 | 5/1992 | Cetenko et al. . |
| 5,229,516 | 7/1993 | Musser et al. . |
| 5,401,774 | 3/1995 | Pamukcu et al. . |
| 5,420,289 | 5/1995 | Musser et al. . |

FOREIGN PATENT DOCUMENTS

| | | |
|---|---|---|
| 61-106521 | 5/1986 | Japan . |
| 1178658 | 1/1970 | United Kingdom . |
| 91/06537 | 5/1991 | WIPO . |
| 96/03120 | 2/1996 | WIPO . |
| 96/03987 | 2/1996 | WIPO . |

OTHER PUBLICATIONS

Waddell, W.R. et al., Am. J. Surgery, vol. 157, pp. 175–179 (1989).
Gonzaga, R.A.F. et al., The Lancet, Mar. 30, 1985, p. 751.
Waddell, W.R. et al., J. Surg. Oncology, vol. 24, pp. 83–87 (1983).
Federation Proceedings (1972) of the Federation of American Societies for Experimental Biology abstract Nos. 2044 and 2045.
Gilman, S.C. et al., Nonsteroidal Anti–inflammatory Drugs in Cancer Therapy, (circa 1985).
Brogden, R.N. et al., Drugs, vol. 16, pp. 97–114 (1978).
Hucker, H.B. et al., Drug Metabolism & Disposition, vol. 1, No. 6, pp. 721–736 (1973).
Shen, T.Y. et al., Chemical and Biological Studies on Indomethacin, Sulindac and Their Analogs, pp. 107–178 (circa 1975).
Duggan, D.E. et al., Clin. Pharm. & Therapeutics, vol. 21, No. 3, pp. 326–335 (1976).
Duggan, D.E. et al., J. Pharm. & Exper. Therap., vol. 201, No. 1, pp. 8–13 (1977).
Glavin, G.B. et al., Toxicology and Applied Pharmacology, vol. 83, pp. 386–389 (1986).
Moorghen, M. et al., Journal of Pathology, vol. 156, pp. 341–347 (1988).
Bjarnason et al., Gastroenterology, vol. 94, No. 4, pp. 1070–1074 (1988).

*Primary Examiner*—Paul J. Killos
*Attorney, Agent, or Firm*—Robert W. Stevenson

[57] ABSTRACT

Substituted condensation products of 1H-indenylhydroxyalkanes with aldehydes are useful for inducing or promoting apoptosis and for arresting uncontrolled neoplastic cell proliferation, and are specifically useful in the arresting and treatment of neoplasia, including precancerous and cancerous lesions.

52 Claims, No Drawings

6,028,116

SUBSTITUTED CONDENSATION PRODUCTS OF 1H-INDENYL-HYDROXYALKANES WITH ALDEHYDES FOR NEOPLASIA

TECHNICAL FIELD

This invention relates to compounds and methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical displasia (cervical cancer) and other such neoplasms.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because whatever cancer preventative (as opposed to cancer-fighting) capabilities those drugs may possess, they do not outweigh their severe side effects. Most standard chemotherapeutics are now believed to kill cancer cells by inducing apoptosis (also sometimes referred to as "programmed cell death"). Apoptosis naturally occurs in many tissues in the body. Apoptosis plays a critical role in tissue homeostasis, that is, it ensures that the number of new cells produced are offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect the intestinal lining against overgrowth.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulcerations and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which causes gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans. Thus, the severe side effects due to induction of apoptosis in normal cells by conventional chemotherapeutics are avoided by these novel therapeutics (see, Van Stock, et al., *Gastroenterology* 112 (4): A673, 1997). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents potent compounds that induce apoptosis in neoplastic cells (but not substantially in normal cells), for treating patients with neoplastic lesions without substantially inhibiting PGE-2. This invention also involves methods for inducing such specific apoptosis in neoplastic cells by exposing such cells to a pharmacologically effective amount of those compounds described below to a patient in need of such treatment. Such compositions are effective in modulating apoptosis and modulating the growth of neoplasms, but are not causing the side effects of conventional chemotherapeutics and NSAIDs.

In addition, compounds of this invention are active pro-drugs of active metabolites. In other words, the compounds of Formula I below are potent specific inhibitors of neoplasia that metabolize into compounds that are also specific inhibitors of neoplasia.

DETAILED DESCRIPTION OF THE INVENTION

As discussed above, the present invention includes compounds of Formula I below (as well as their pharmaceutically acceptable salts) for treating a patient with neoplastic, particularly precancerous, and cancerous lesions:

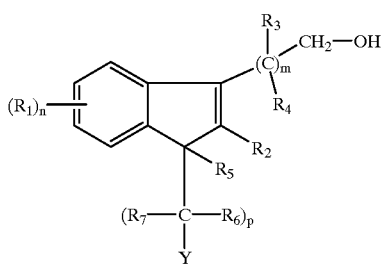

wherein
- $R_1$ is independently selected in each instance from the group consisting of hydrogen, halogen, lower alkoxy, hydroxy, lower alkyl, lower alkyl mercapto, lower alkylsulfonyl, lower alkylamino, di-lower alkyl amino, amino, nitro, nitrile, lower alkyl carboxylate, —$CO_2H$, and sulfonamido;
- $R_2$ is selected from the group consisting of hydrogen and lower alkyl; $R_3$ and $R_4$ are independently selected from the group consisting of hydrogen, hydroxy, amino, lower alkyl amino, alkylamino alkyl, lower alkyl, lower alkoxy, hydroxyalkyl, lower alkylmercapto, and lower alkylsulfonyl;
- $R_5$ is selected from the group consisting of hydrogen and hydroxy, or $R_5$ and $R_6$ together form a double bond;
- $R_6$ is selected from the group consisting of hydrogen and hydroxy, or $R_6$ and $R_7$ together form an oxygen when $R_5$ and $R_6$ together do not form a double bond;
- $R_7$ is selected from the group consisting of hydrogen, amino, lower alkyl amino, di-lower alkylamino;
- m is an integer from 0 to 3;
- n is an integer from 0 to 4;
- p is an integer from 1 to 3;
- Y is selected from the group consisting of phenyl, quinolinyl, isoquinolinyl, pyridinyl, pyrimidinyl, pyrazinyl, imidazolyl, indolyl, benzimidazolyl, triazinyl, tetrazolyl, thiophenyl, furanyl, thiazolyl, pyrazolyl, or pyrrolyl, or substituted variants thereof wherein the substituents are one to three independently selected from the group consisting of halogen, lower alkyl, lower alkoxy, amino, lower alkylamino, di-lower alkylamino, hydroxy, nitro, nitrile, —$CO_2H$, —$SO_2NH_2$, lower alkyl mercapto, and lower alkyl sulfonyl; and pharmaceutically acceptable salts thereof.

Preferred compounds of Formula I include those where $R_1$ is selected from the group consisting of halogen, lower alkoxy, lower alkylsulfonyl, lower alkyl amino, di-lower alkyl amino, amino, lower alkylcarboxylate, —$CO_2H$, and sulfonamido; $R_2$ is lower alkyl; $R_3$ and $R_4$ are independently selected from the group consisting of hydrogen, hydroxy, amino, lower alkylamino, alkylaminoalkyl and lower alkylsulfonyl; $R_5$ is hydroxy; $R_6$ is hydrogen, or $R_5$ and $R_6$ together form a double bond; $R_7$ is hydrogen or amino; m is 1; n is 1–3; p is 1 or 2; and Y is phenyl, quinolinyl, isoquinolinyl, pyridinyl, pyrimidinyl, pyrazinyl, imidazolyl, indolyl, benzimidazolyl, triazinyl, or tetrazolyl; the substituents on the "Y" ring are independently selected from the group consisting of halogen, lower alkoxy, di-loweralkylamino, amino or hydroxy.

Still more preferred compounds of this invention include those of Formula I where $R_1$ is selected from the group consisting of halogen, lower alkoxy, lower alkylsulfonyl, lower alkyl amino, di-lower alkyl amino, and amino; $R_2$ is lower alkyl; $R_3$ and $R_4$ are independently selected from the group consisting of hydrogen, hydroxy, and amino; $R_5$ is hydroxy; $R_6$ is hydrogen, or $R_5$ and $R_6$ together form a double bond; $R_7$ is hydrogen; m is 1; n is 1–2; p is 1; and Y is phenyl, quinolinyl, isoquinolinyl, pyridinyl, pyrimidinyl or pyrazinyl; the substituents on the "Y" ring are independently selected from the group consisting of halogen, lower alkoxy, di-loweralkylamino, amino or hydroxy.

The most preferred group of compounds within Formula I are those where $R_1$ is halogen, particularly 5-fluoro or chloro; $R_2$ is lower alkyl; $R_3$ and $R_4$ are identical, particularly where both are hydrogen; $R_5$ and $R_6$ together form a double bond; $R_7$ is hydrogen; m, n and p are 1; and Y is phenyl; the substituents on the "Y" ring are independently selected from the group consisting of halogen, lower alkoxy, and di-loweralkylamino.

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

Also, the present invention is a method of inhibiting the growth of neoplastic cells by exposing the cells to an effective amount of compounds of Formula I, wherein $R_1$, $R_2$, $R_3$, $R_4$, $R_5$, $R_6$, $R_7$, m, n, p, and Y are defined as above.

In still another form, the invention is a method of inducing apoptosis in human cells by exposing those cells to an effective amount of compounds of Formula I, wherein $R_1$ through $R_7$ m, n, p, and Y are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ through $R_7$ etc. are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "lower alkyl carboxylate" refers to a carboxylate group that is substituted with a lower alkyl group.

The term "hydroxyalkyl" refers to a lower alkyl group substituted with 1–3 hydroxy groups.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enaniomers may be synthesized from chiral starting materials, or the racemates can be resolved by conventional procedures that are well known in the art of chemistry such as chiral chromatography, fractional crystallization of diastereomeric salts and the like.

Compounds of Formula I also can exist as geometrical isomers (Z and E); the Z isomer is preferred.

Compounds of this invention may be formulated into pharmaceutical compositions together with pharmaceutically acceptable carriers for oral administration in solid or liquid form, or for rectal, intravenous, or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel. Pharmaceutically acceptable carriers for intraveneous administration include solutions containing pharmaceutically acceptable salts or sugars.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

There are several general schemes for producing compounds useful in this invention.

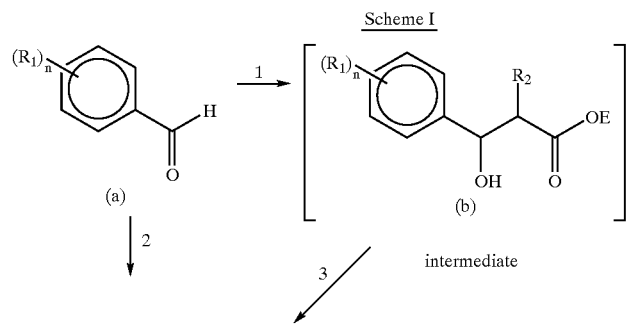

Scheme I

-continued
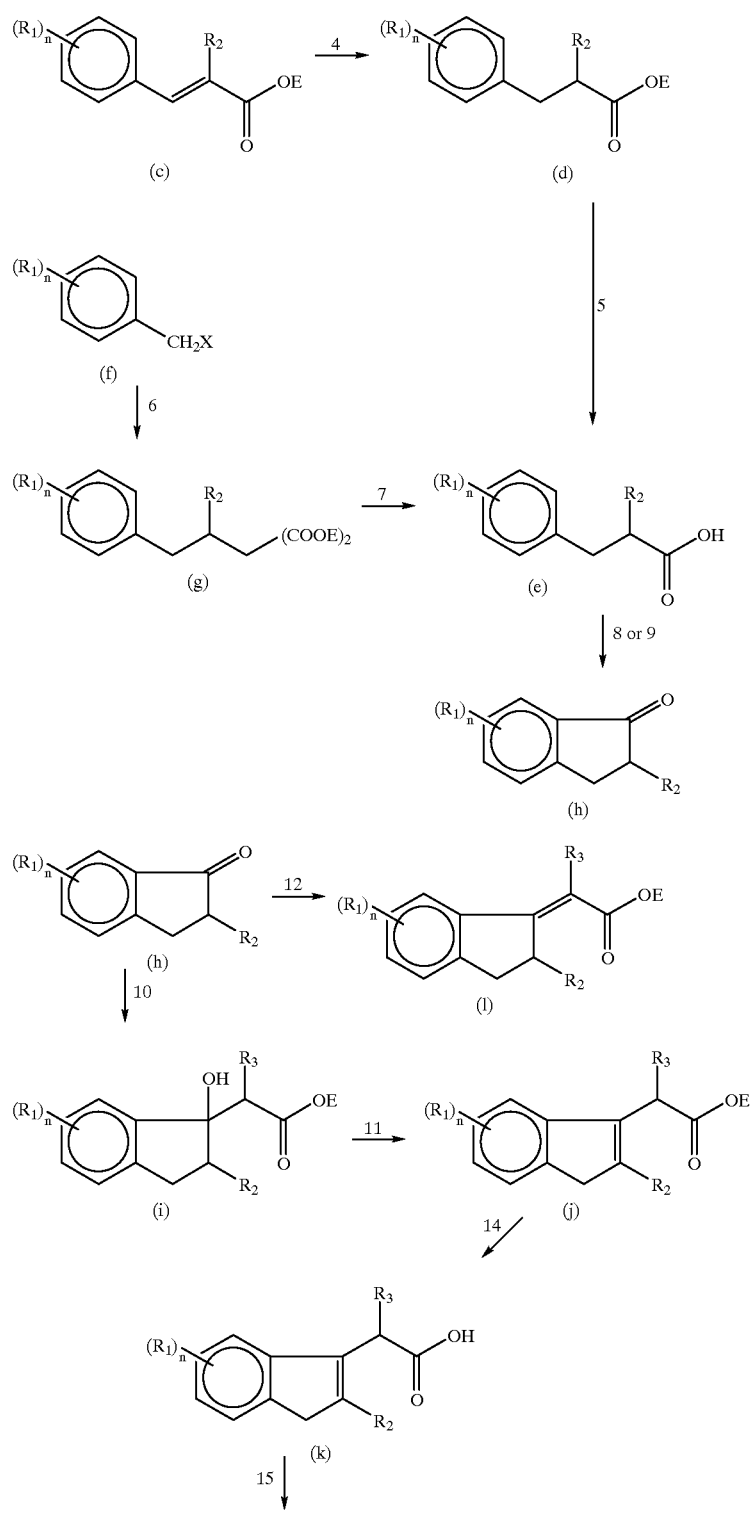

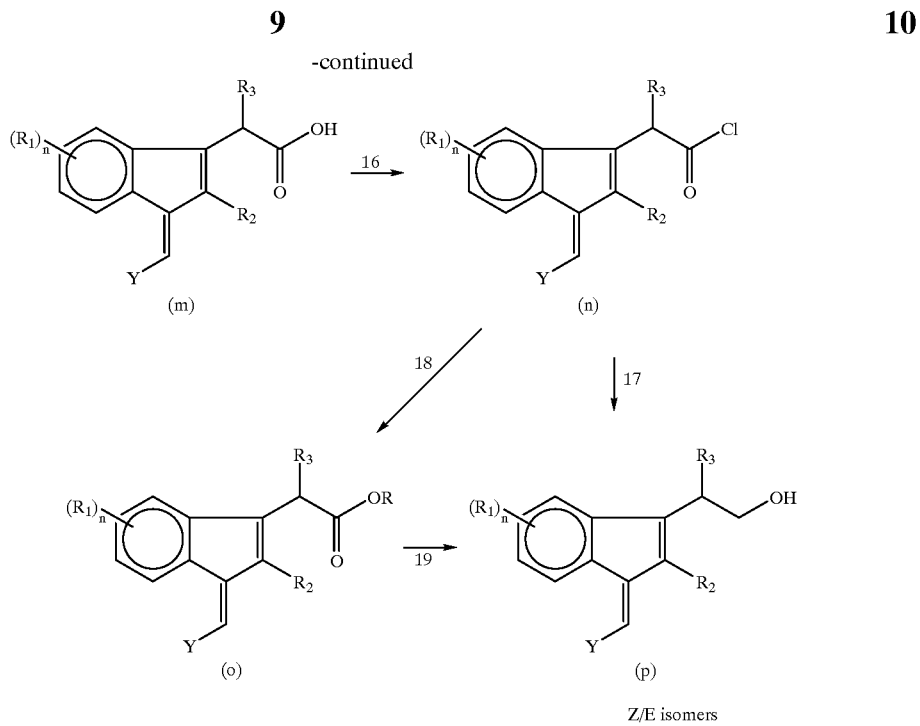

Z/E isomers

In Scheme I, several sub-variations can be used. In one sub-variation, a substituted benzaldehyde (a) may be condensed with a substituted acetic anhydride (resp. ester) in a Perkin reaction (see, reaction 1) or with an α-halogeno propionic ester in a Reformatsky dehydration reaction (see, reactions 1 and 3). The resulting cinnamic acid (resp. ester) (c) is hydrogenated and hydrolyzed to give a substituted benzyl propionic acid (e) (see reactions 4 and 5). Alternatively, a substituted malonic ester (g) from a typical malonic ester synthesis (see, reactions 6 and 7), after hydrolytic decarboxylation of the resulting substituted ester (g) yields the benzyl propionic acid (e). This latter method is especially preferable if there are nitro and alkylthio substituents on the benzene ring.

The next step is the ring closure of the β-aryl propionic acid (e) to form an indanone (h) which may be carried out by a Friedel-Crafts Reaction using a Lewis acid catalyst (Cf. Organic Reactions, Vol. 2, p. 130) or by heating with polyphosphoric acid (see reactions 8 and 9, respectively). In the indanone (h), the carboxyl oxygen may be replaced by a carboxyalkylidene side chain via a Reformatsky dehydration reaction sequence (see, reaction 10). Alternatively, this replacement can be carried out by the use of a Wittig Reaction in which the reagent is a α-triphenylphosphinyl ester (see reaction 12). This product (i) is then immediately rearranged to the indene (j) (see reaction 13). If the Reformatsky Reaction route is used, the intermediate 3-hydroxy-3-aliphatic acid derivative (i) must be dehydrated to the indene (j) (see reaction 11).

In reaction 14, the ester (j) is saponified with NaOH and acidified with HCl to the acid (k). The acid (k) is then condensed with a substituted aldehyde (see reaction 15) to produce the indenylacetic acid (m).

Subsequently, the indenylacetic acid (m) in THF is allowed to react with oxalyl or thionyl chloride or similar reagents to produce the acid chloride (n) (see reaction 16), whereupon the solvent is evaporated. There are two methods to carry out reaction 17, which is the reduction to the primary alcohol (p).

Method (I)—Reaction 17

Reduction of the acid chloride (n) with lithium borohydride in tetrahydrofuran takes place at room temperature or in an ice bath. The reaction is quenched with water or aqueous hydrochloric acid and extracted. The organic phase is dried ($K_2CO_3$) and is evaporated to give the alcohol (p).

Method (II)—Reactions 18/19

In the second method, the acid chloride (n) reacts with an alcohol (ROH; where R is preferably lower alkyl) and forms an ester (o) which is then reduced (e.g., with $LiBH_4$ in THF) to the primary alcohol (p) (see reaction 19).

To summarize Scheme I, the reagents and general conditions for the Scheme (numbers refer to the numbered reactions) are as follows:

(1) Br—CH($R_2$)—COOE; $R_2CH_2$—COONa, ΔT, Zn in anhydrous inert solvent, where E=H.
(2) ($R_2CH_2CO)_2O$ where E=lower alkyl
(3) $KHSO_4$ or p-toluene sulfonic acid.
(4) $H_2$ palladium on charcoal, 40 p.s.i. room temperature.
(5) NaOH in aqueous alcohol at 20–100° C.
(6) $NaOC_2H_5$ or any other strong base such as NaH or K-t-butoxide.
(7) A) Base B) Acid
(8) Friedel-Crafts Reaction using a Lewis Acid catalyst Cf. Organic Reactions. Vol. II, p. 130.
(9) Heat with polyphosphoric acid.
(10) Reformatsky Reaction: Zn in inert solvent, heat, X—CH($R_3$)—COOE.
(11) p-Toluene sulfonic acid and $CaCl_2$ or 12 at 200° C.
(12) Wittig Reaction using $(C_6H_5)_3P=C$—COOE 20–80° C. in ether or benzene
(13) (a) $NBS/CCl_4$/benzoyl peroxide (b) $PtO_2/H_2$ (1 atm.)/ acetic acid
(14) (a) NaOH (b) HCl
(15) Substituted aldehyde, acid (e.g., HCl)
(16) Oxalyl or thionyl chloride in $CH_2Cl_2$ or THF
(17) $LiBH_4$/THF, acid (Method I)
(18) ROH (Method II) Formation of an Ester
(19) $LiBH_4$/THF, acid Alternatively, step 16 can be carried out with a nucleophilic fluorinating reagent. The resulting acid fluoride can be reduced in step 17 with NaBH$_4$ (JOC 1996, 61, 6994–6996).

Indanones of the general structure (h) in scheme I are known in the literature and are available precursors so that reactions 1–7 can be conveniently avoided. Among such known indanones are:
5-methoxyindanone
6-methoxyindanone
5-methylindanone
5-methyl-6-methoxyindanone
5-methyl-7-chloroindanone
4-isopropyl-2,7-dimethylindanone
5,6,7-trichloroindanone
2-n-butylindanone
5-methylthioindanone Scheme I described above for simplicity illustrates the case where m is 1. To produce compounds within the scope of this invention where m is 2 or 3, the following scheme IA can be employed.

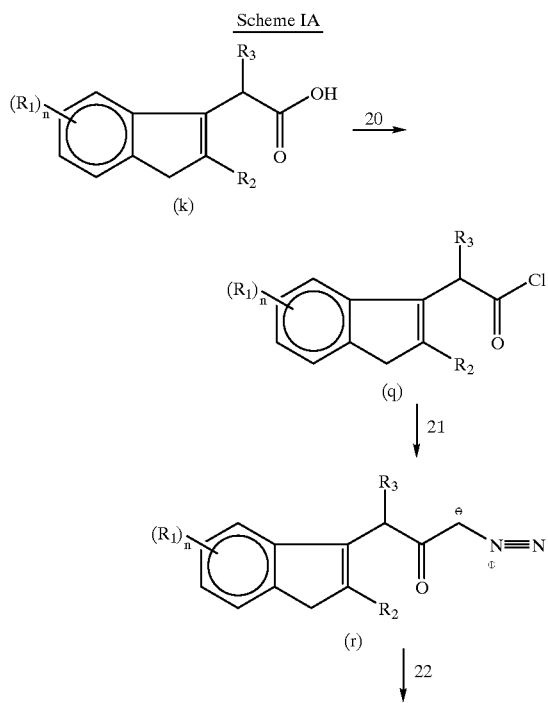

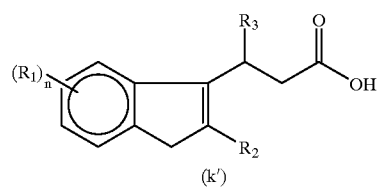

In Scheme IA, the Arndt-Eistert reaction of the acid chloride (q)(from compound k by reaction 20) with diazomethane produces the substituted indenyl diazomethyl ketone (r) (see reaction 21).

Compound (r) is treated with silver oxide in ethanol followed by base (e.g., NaOH) and acid treatment (see reaction 22) to produce the indenyl propionic acid (k') that can be used in Scheme I above in place of compound (k) in the reaction sequence 15–17 to give the propionic alcohols.

To produce higher substituted or unsubstituted alcohols (e.g., butanol derivatives), reactions 20–22 are repeated using the previously synthesized acid (e.g., compound k') as a starting material. Homologous acids can be used in Scheme I above in place of compound k in reaction 15.

Conditions for the scheme 1A (numbers refer to numbered reactions) are as follows:

(20) oxalylchloride or thionylchloride or CH$_2$Cl$_2$ or THF

(21) CH$_2$N$_2$

(22) Ag$_2$O/EtOH; 2N NaOH; HCl

For substituted and unsubstituted benzylidene indenyl acetic, propionic or butyric acids (i.e., where Y is a substituted or unsubstituted aryl), the preferred reaction scheme involves reactions 16–19 of Scheme I. To produce compounds useful in this invention where Y is other than aryl (e.g., where Y is one of the above-mentioned substituted or unsubstituted heterocycles), Scheme II below is employed.

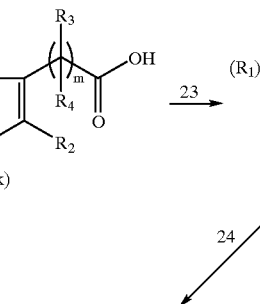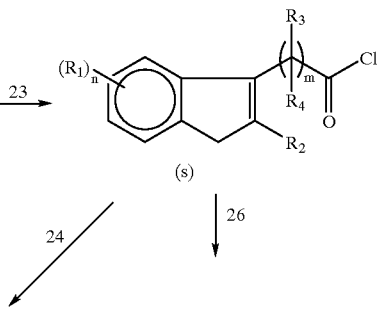

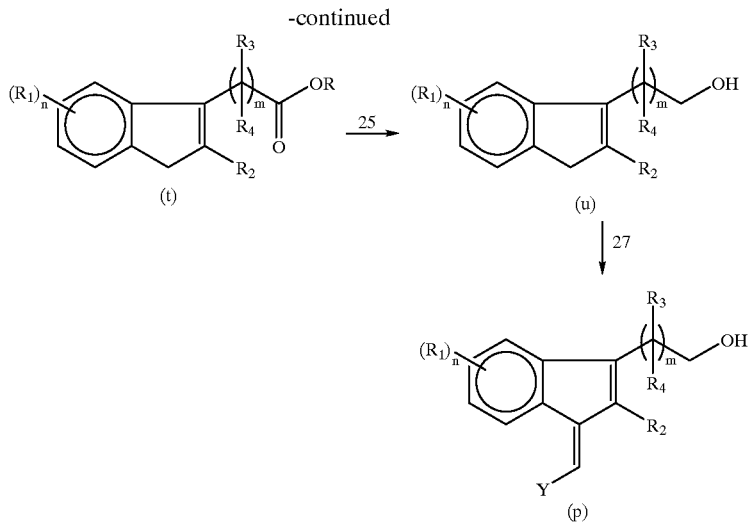

In Scheme II, compound (k) (or compound k') is allowed to react with oxalylchloride or thionyl chloride in dichloromethane (see reaction 23) to give the acid chloride (s), which is then used to produce the substituted primary alcohol (u) by either of two methods: by reaction sequence 24–25 or by reaction 26.

In method I (reaction 26), compound (s) is reduced with lithium borohydride in tetrahydrofuran, then acidified (e.g., with hydrochloric acid) to give compound (u).

In method II, compound (s) is allowed to react with a lower alcohol (i.e., ROH where R is lower alkyl, preferably methyl) to produce the substituted ester (t), which is then reduced with lithium borohydride to give the primary alcohol (u) (see reaction 25).

To produce a primary alcohol (p), with a heterocycle in position one of the indene core, compound (u) is allowed to react with a heterocyclic aldehyde (i.e., Y—C(O)—HE, where Y is one of the above-mentioned heterocycles) in a Wittig reaction (27) in order to produce a primary alcohol (p) with a heterocycle in position one.

To create variants of compound p (produced either by Schemes I or II) where $R_5$, $R_6$ and $R_7$ (see Formula I) are other than hydrogen, other procedures are preferably used.

When $R_5$ is a hydroxy group, Scheme III is employed.

Scheme III

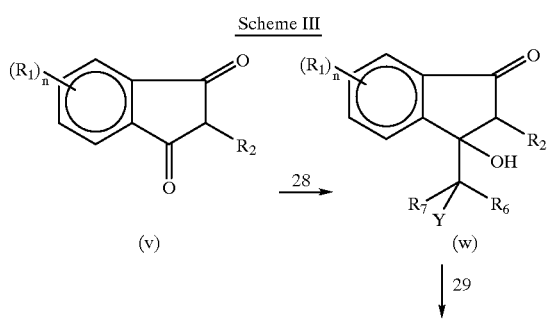

Starting with the 1,3-indandione (h) (Lit. Synthesis 15, 1994, 1083–1086) the "Y—$(CR_6R_7)_p$—" substituent is introduced by a Grignard Reaction. If $R_6$ or $R_7$ is a Grignard-labile group (e.g., NHR, OH, or $NH_2$), it should be protected prior to being subjected to reaction 28 (for example, a protecting group such as methyl carbamate can be used) and deprotected after the Grignard Reaction (e.g., cleavage of the methylcarbamate with HBr/acetic acid).

After the Grignard Reaction (28), the protected tertiary alcohol (w) is allowed to react with methylbromoacetate in the presence of zinc amalgam as a catalyst.

Workup with base and acid yields the acetic acid (x) (see reaction 29) which is transformed to the methylester (y) by reaction with diazomethane (reaction 30). Reduction of the methylester with lithium borohydride leads after acidic workup to the primary alcohol (p') (see reaction 31).

When $R_6$ and $R_7$ form a ketogroup, or $R_6$ is a hydroxygroup or an amine and $R_7$ is hydrogen, Scheme IV is employed.

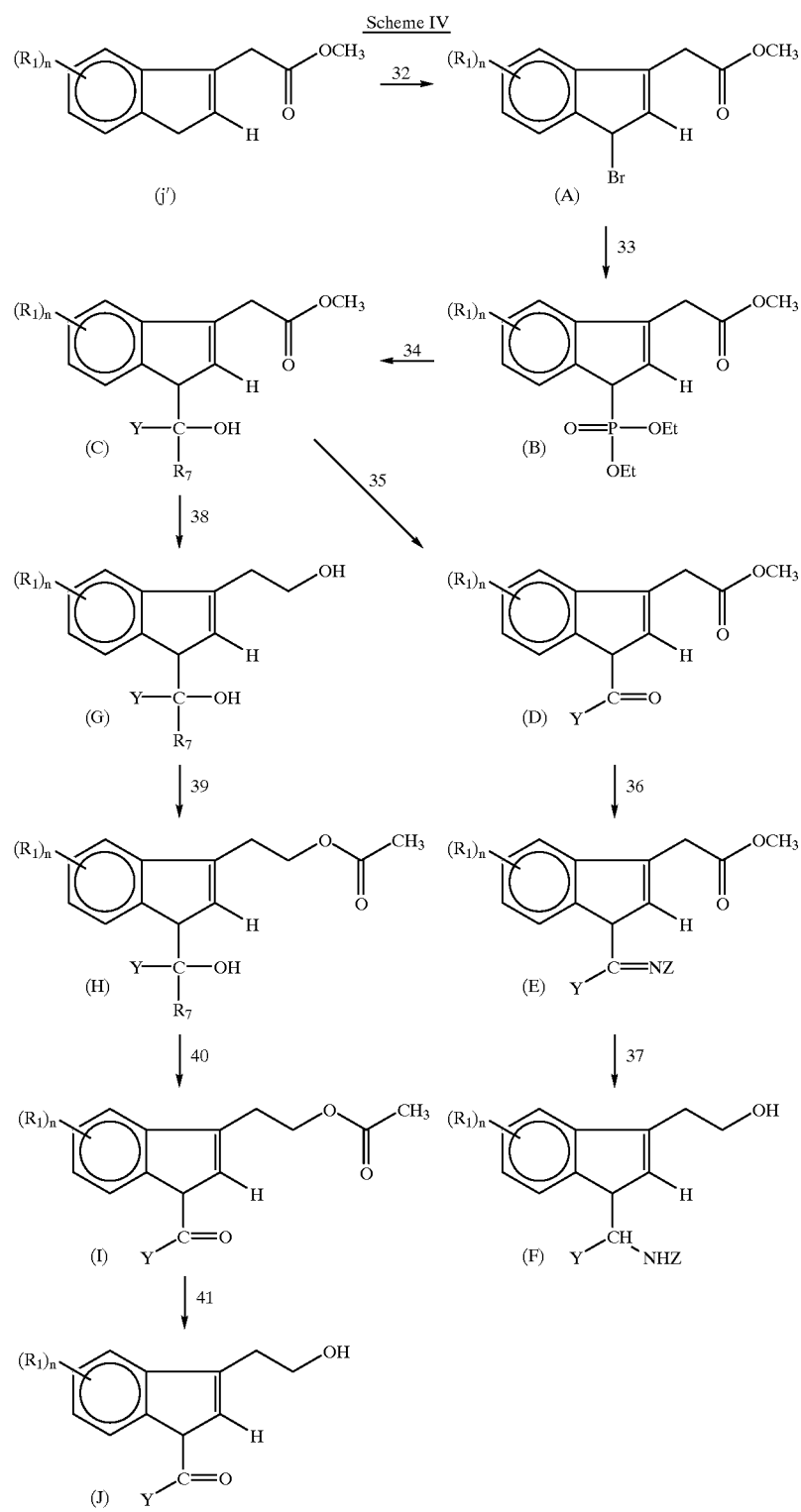

A dibenzoylperoxide-induced radical reaction of the methylester (j') with N-bromo-succinamide in carbontetrachloride leads to the bromo-substituted methylester (A) (see reaction 32).

The methylester (A) reacts with triethylphosphate (reaction 33) to give the phosphonate. A Homer Emmons Reaction of the phosphonate (B) (reaction 34) produces the tertiary alcohol (C) which is oxidized with potassium dichromate to the ketone (D) (reaction 35). Reaction of the ketone (D) with an amine (Z—$NH_2$ where Z is a lower alkyl or hydrogen) leads to an imine (E) (reaction 36), which can then be reduced with lithium aluminum hydride to the corresponding amine (F) (reaction 37). Starting with the alcohol (C), its methylester substituent can be reduced with lithium borohydride to the primary alcohol. Acidic workup leads to the diol (G) (reaction 38). Acetylation with ethylacetate over silicagel protects the primary alcohol of (G) and yields the alcohol (H) (reaction 39). The alcohol (H) is oxidized with potassium dichromate (reaction 40) to the ketone (I) and its ester group is then saponified to yield the primary alcohol (J) (reaction 41).

In summary, the reagents and general conditions of Schemes II, III and IV are as follows (numbers refer to numbered reactions):

(23) oxalyl or thionyl chloride in $CH_2Cl_2$ or THF
(24) ROH, formation of the ester
(25) $LiBH_4$/THF, acid
(26) $LiBH_4$/THF, acid
(27) Substituted benzaldehyde or heterocyclic aldehyde, acidic or basic workup conditions
(28) Grignard reagent (Y—$CR_6R_7$—MgHal)
(29) (a) Bromomethyl acetate, Zn-amalgam, base (b), acid
(30) $CH_2N_2$
(31) $LiBH_4$/THF, acidic workup
(32) Dibenzoylperoxide, heat, N-Bromo-succinimide in $CCl_4$
(33) Triethoxyphosphate (Synthesis: TL, 26, 1986, 2391)
(34) Homer-Emmons Reaction: NaH, Y—C(O)—$R_7$ (Synthesis, 1994, 1083; J.O.C. 1994, 59, 6887–89)
(35) $K_2Cr_2O_7$
(36) Z—$NH_2$, with Z-lower alkyl or hydrogen
(37) $NaBH_4$
(38) $LiBH_4$/THF, acidic workup
(39) Silicagel, ethylacetate (J.O.C. 1997, 62, 8952–8954)
(40) $K_2Cr_2O_7$
(41) NaOH

EXAMPLE 1

(Z)-5-Fluoro-2-Methyl-1-(4-Methylthio-Benzylidene)-1H-3-Indenyl-(2-Hydroxy)Ethane (A) p-Fluoro-α-methylcinnamic acid p-Fluorobenzaldehyde (200 g, 1.61 mol), propionic anhydride (3.5 g, 2.42 mol) and sodium propionate (155 g, 1.61 mol) are mixed in a nitrogen-flushed 1 l three-necked flask. The flask is heated gradually in an oil-bath to 140° C. After 20 hours, the contents are cooled to 100° C., and are poured into 8 l of water. The precipitate is dissolved by adding potassium hydroxide (302 g) in water (2 l). The aqueous solution is washed with ether, and the ether layers are re-extracted with potassium hydroxide solution. The combined aqueous layers are filtered, are acidified with concentrated HCl, and are filtered. The collected solid, p-fluoro-α-methylcinnamic acid, is washed with water, and is dried and used as obtained.

(B) p-Fluoro-α-methylhydrocinnamic acid

5% Pd/C (11.0 g) is added to p-fluoro-α-methylcinnamic acid (177.9 g, 0.987 mol) in 3.6 l ethanol. The mixture is hydrogenated at room temperature at 40 p.s.i. When the hydrogen uptake ceases, the catalyst is filtered off, and the filtrate is concentrated in vacuo to give the product, p-fluoro-α-methylhydrocinnamic acid, which is used without weighing in the next step.

(C) 6-Fluoro-2-methylindanone p-fluoro-α-methylhydrocinnamic acid (93.2 g, 0.5 mol) is added slowly to 932 g polyphosphoric acid at 70° C. (on the steam bath). The temperature is gradually raised to 95° C., and the mixture is kept at this temperature for 1 hour. The aqueous solution is extracted with ether. The ether solution is washed twice each with water, with 5% $Na_2CO_3$, and with aqueous saturated NaCl, is dried, and is concentrated with 200 g silica-gel. The slurry is added to a five pound silica-gel column packed with 5% ether-petroleum ether. The column is eluted with 5–10% ether-petroleum ether, to give 6-fluoro-2-methylindanone. Elution is monitored by TLC.

(D) 5-Fluoro-2-methylinden-3-yl acetic acid

A mixture of 6-fluoro-2-methylindanone (18.4 g, 0.112 mol), cyanoacetic acid (10.5 g, 0.123 mol), acetic acid (6.6 g), and ammonium acetate (1.7 g) in dry toluene (15.5 ml) is refluxed for 21 hours, as the liberated water is collected in a Dean Stark trap. The mixture is evaporated to dryness, and the residue is dissolved in hot ethanol (60 ml) and 2.2 N aqueous potassium hydroxide solution (14 ml). 85% KOH (22 g) in water (150 ml) is added, and the mixture is refluxed for 13 hours under nitrogen. The ethanol is removed in vacuo, and water (500 ml) is added. The aqueous solution is washed well with ether and is boiled with charcoal, and is filtered. The aqueous filtrate is acidified to pH 2 with 50% cold hydrochloric acid. The precipitate yields the title compound, 5-fluoro-2-methylinden-3-yl acetic acid (m.p. 164–166° C.).

(E) (Z)-5 Fluoro-2-methyl-1-(4-methylthiobenzylidene)-3-indenylacetic acid

5-Fluoro-2-methylinden-3-yl acetic acid (15 g, 0.072 mol), p-methylthiobenzaldehyde (14.0 g, 0.091 mol) and sodium methoxide (13.0 g, 0.24 mol) are heated in methanol (200 ml) at 60° C. under nitrogen with stirring for 6 hours. After cooling, the reaction mixture is poured into ice-water (750 ml), and is acidified with 2.5N hydrochloric acid. The collected solid is triturated with a little ether to produce (Z)-5-fluoro-2-methyl-1-(4-methylthiobenzylidene)-3-indenylacetic acid (m.p. 187–188.2° C.).

(F) (Z)-5-Fluoro-2-methyl-1-(4-methylthiobenzylidene)-3-indenylacetyl chloride (Z)-5-fluoro-2-methyl-1-(4-methythiobenzylidene)-3-indenylacetic acid (70 mmol) in THF (500 ml) is allowed to react with oxalylchloride (2 M in $CH_2Cl_2$; 35 ml) under reflux conditions (24 hours). The solvent is evaporated to yield the title compound, which is used as such in the next step.

(G) (Z)-5-Fluoro-2-methyl-1-(4-methylthiobenzylidene)-1H-3-indenyl-(2-hydroxy)ethane Lithium borohydride (1.38 mmol) in THF (2 ml) is added to the solution of (Z)-5-fluoro-2-methyl-1-(4-methyl thiobenzylidene)-3-indenylacetyl chloride (2.78 mmol) in THF (20 ml) at 0° C. The reaction is quenched after 5 minutes with 10%, aqueous HCl (30 ml). Ethyl acetate (50 ml) is added to extract the product.

The organic layer is washed with water (2×50 ml), is dried over $Na_2SO_4$ and is evaporated to give a residue, which is purified by flash chromatography to give (Z)-5-Fluoro-2-methyl-1-(4-methylthiobenzylidene)-1H-3-indenyl-(2-hydroxy)ethane (ethylacetate:hexane 8:2). ($R_1$=F, $R_2$=$CH_3$, $R_3$=H, $R_4$=H, Y=4-methylthiophenyl, n=1, $R_5$ and $R_6$ form a double bound, $R_7$=H, m=1, p=1).

Formula: $C_{20}H_{19}FOS$.

Molecular Mass: 326.42 g/mol.

Melting point: 88° C.

$^1$H-NMR [ppm] ($CDCl_3$): 2.19 (s,3, —$CH_3$); 2.55 (s,3, $CH_3$S); 2.84 (t,2,$CH_2$); 3.84 (t,2,$CH_2$O); 6.55–7.38 (m,3, ar.); 7.11 (s,1, =CH—); 7.28–7.45 (AB,4,Ph—S).

IR [cm$^{-1}$](KBr): 3300 O—H; 1165 C—F.

EXAMPLE 2

(Z)-5,6-Difluoro-2-Methyl-1-(4-Methylthiobenzylidene)-1H-3-Indenyl-(2-Hydroxy)Ethane (A) 3,4-Difluorobenzaldehyde 3,4-difluorotoluene (25.6 g, 0.2 mol) is heated to 105° C. in a 250 ml 3-necked flask equipped with a magnetic stirrer, thermometer, condenser, and dropping funnel, and is illuminated as bromine (67 g, 0.42 mol) is added slowly. The temperature is kept between 105–110° C. while the first half of the bromine is added over a period of one hour. The rest of the bromine is added over approximately a two-hour period, and the temperature is raised to 150° C., and is kept there for 5 minutes. The reaction mixture is cooled and is transferred to a 1 liter 3-necked flask with a motor-driven stirrer and condenser. H$_2$O (120 ml) and calcium carbonate (90 g) are added, and the mixture is refluxed for 20 hours with good stirring. The reaction mixture is steam distilled until no further oil is collected. The oil is taken up in methylene chloride and dried over MgSO$_4$. Evaporation of the solvent yields 3,4-difluorobenzaldehyde that is used without further purification.

(B) 3,4-Difluoro-α-methylcinnamic acid

A mixture of 3,4-difluorobenzaldehyde (2.88 g, 0.02 mol), propionic anhydride (3.24 g, 0.025 mol) and sodium propionate (0.92 g, 0.02 mol) under nitrogen is heated to 135° C. for 20 hours. The reaction mixture is poured into water (50 ml). A solid precipitates, which dissolves when saturated K$_2$CO$_3$ (50 ml) is added with stirring. The basic solution is washed with ether (2×100 ml). The aqueous phase is poured into an excess of concentrated HCl and ice. The precipitated white solid is filtered and dried to give 3,4-difluoro-α-methylcinnamic acid, m.p. 122–125° C.

(C) 3,4-Difluoro-α-methylhydrocinnamic acid 3,4-difluoro-α-methylcinnamic acid (28 g; 0.141 mol), PtO$_2$ (1 g) in MeOH (250 ml) is hydrogenated at 45 p.s.i. until the theoretical uptake is completed. The catalyst is filtered off, and the material is evaporated to one-third of its original volume. A 15% potassium hydroxide solution (10 ml) is added, and the mixture is refluxed for 30 minutes. It is poured into water and extracted with ether (2×100 ml). The aqueous layer is acidified with concentrated HCl and ice, to produce an oil which is extracted into ether. The ether solution is dried over MgSO$_4$, and is evaporated to leave 3,4-difluoro-α-methylhydrocinnamic acid (m.p. 55–56° C.) as a clear oil which crystallizes.

(D) 5,6-Difluoro-2-methyl-1-indanone 3,4-difluoro-α-methylhydrocinnamic acid (20 g; 0.1 mol) is added to polyphosphoric acid (250 g). The mixture is efficiently stirred and heated on a steam bath for 2 hours, and is then poured into ice water (400 ml). The precipitate is extracted with ether (3×100 ml). The extract is washed with saturated potassium carbonate, and with water, and is dried (MgSO$_4$). The ether solution is evaporated to leave solid 5,6-difluoro-2-methyl-1-indanone (m.p. 66–68° C.) which is used without further purification.

(E) Methyl 5,6-difluoro-2-methylindene-3-acetate

A mixture of 5,6-difluoro-2-methyl-1-indanone (9.1 g (0.05 mol), "activated" zinc dust (4.0 g), methyl bromoacetate (7.6 g; 0.05 mol) and a crystal of iodine in dry benzene (250 ml), is refluxed for 4–5 hours. TLC (20% Et$_2$O/hexanes, 1:4 on SiO$_2$) shows greater than 95% conversion at this time. The reaction mixture is poured into 5% H$_2$SO$_4$, (250 ml). The organic phase is separated and is dried (MgSO$_4$). Removal of solvent leaves an oily hydroxy ester. The solution of the crude ester in benzene (100 ml) is heated at reflux for 30 minutes with phosphorus pentoxide (20 g) and is decanted. The residue is extracted with benzene, the organic layers are combined, are washed with water (2×100 ml), and are dried (MgSO$_4$) and evaporated to yield methyl 5,6-difluoro-2-methylindene-3-acetate (m.p. 86–90° C.).

(F) (Z)-5,6-Difluoro-2-methyl-1-(p-methylthiobenzylidene)-indene-3-acetic acid

Methyl 5,6-difluoro-2-methylindene-3-acetate (1.19 g, 5.0 mmol) in dry pyridine (10 ml) is mixed with p-methylthiobenzaldehyde (0.76 g, 5.0 mmol) under nitrogen. Triton B (5.0 g, 5.1 mmol) is added. The deeply colored solution is allowed to stand overnight. Water (2 ml) is added. After 15 minutes, the mixture is poured into an excess of water. Organic impurities are extracted with ether (2×50 ml). The aqueous phase is added to 10% HCl/ice. The orange gummy solid that precipitates is extracted with methylene chloride. The extract is dried (MgSO$_4$). The solvent is removed to leave an orange solid. The solid that is recrystallized from benzene to yield (Z)-5,6-difluoro-2-methyl-1-(p-methylthiobenzylidene)-indene-3-acetic acid. m.p. 181–182.5° C.

(G) (Z)-5,6-Difluoro-2-methyl-1-(4-methylthiobenzylidene)-3-indenylacetyl chloride The title compound is obtained according to the procedure of Example 1, Part F.

(H) (Z)-5,6-difluoro-2-methyl-1-(4-methylthiobenzylidene)-1H-3-indenyl-(2-hydroxy)ethane The title compound is obtained according to the procedure of Example 1, Part G. (R$_1$=5,6 difluoro; R$_2$=CH$_3$; R$_3$=H; R$_4$=H; n=2; Y=4-methylthiopheyl, R$_5$ and R$_6$ form a double bond, R$_7$=H, m=1, p=1)

EXAMPLE 3

(Z)-1-(4-Methylthiobenzylidene)-5-Dimethylamino-2-Methyl-1H-3-Indenyl-(2-Hydroxy)Ethane (A) Methyl 3-hydroxy-2-methyl-5-nitro-3-indenylacetate A solution of 2-methyl-6-nitroindanone (13.4 g) and methyl bromoacetate (19.3 g) in benzene (45 ml) is added over a period of 5 minutes to zinc amalgam (21 g) (prepared according to Org. Syn. Coll., Vol. 3) in benzene (110 ml) and dry ether (40 ml). A few crystals of iodine are added to start the reaction. The reaction mixture is maintained at reflux temperature (ca. 65° C.) with external heating. At three-hour intervals, two batches of zinc amalgam (10 g) and bromoester (10 g) are added, and the mixture is refluxed for 8 hours. After addition of ethanol (30 ml) and acetic acid (150 ml), the mixture is poured into 1:1 aqueous acetic acid (700 ml). The organic layer is separated, and the aqueous layer is extracted twice with ether. The combined organic layers are washed thoroughly with water, ammonium hyroxide and water and are dried over sodium sulfate. Evaporation of solvent in vacuo is followed by pumping at 80° C. (bath temp.) (1–2 mm) to give the hydroxy ester product.

A mixture of the above crude hydroxyester, p-toluenesulfonic acid (20 g) monohydrate and anhydrous calcium chloride (20 g) in toluene (250 ml) is refluxed overnight. The solution is filtered, and the solid residue is washed with benzene. The combined benzene solution is washed with water, sodium bicarbonate, and water, and is dried over sodium sulfate. After the mixture is condensed, ethanol (30 ml) and acetic acid (50 ml) are added. The mixture is then poured into water (700 ml). Extraction with ether gives methyl 3-hydroxy-2-methyl-5-nitro-3-indenylacetate.

(B) Methyl 5-dimethylamino-2-methyl-3-indenylacetate

A solution of methyl 3-hydroxy-2-methyl-5-nitro-3-indenylacetate (0.05 mol), 38% aqueous formaldehyde (0.02 mol) and acetic acid (2 ml) in ethanol (100 ml) is reduced catalytically in the presence of a 10% Pd/C catalyst under 40 lb. p.s.i. hydrogen pressure at room temperature. The solution is filtered, evaporated and chromatographed on silica gel (300 g) to give methyl 5-dimethylamino-3-hydroxy-2-methyl-3-indenylacetate. The hydroxy ester is then dehydrated to methyl 5-dimethylamino-2-methyl-3-indenylacetate.

(C) (Z) 1-(p-Methylthiobenzylidene)-5-dimethylamino-2-methyl-3-indenyl acetic acid A solution of the ester (2.5 g) from Part B of this example in 1,2-dimethoxyethane (15 ml) is treated with potassium t-butoxide (1.1 g) and p-methythiobenzaldehyde (1.5 g) in an ice-bath for 4 hours, and is kept at room temperature for 18 hours, and is diluted with ether (15 ml). The potassium salt is filtered off, and is dissolved in water (30 ml), and is neutralized with diluted hydrochloric acid to pH 6–6.5. The precipitate is collected by filtration and is chromatographed with ether-hexanes (1:2; $SiO_2$) as eluent to give pure (Z)-1-(p-methylthiobenzylidene)-5-dimethylamino-2-methyl-3-indenylacetic acid.

(D) (Z)-1-(4-Methylthiobenzylidene)-5-dimethylamino-2-methyl-3-indenylacetyl chloride (Z)-1-(p-methylthiobenzylidene)-5-dimethylamino-2-methyl-3-indenylacetic acid (70 mmol) in THF (500 ml) is allowed to react with oxalylchloride (2 M in $CH_2Cl_2$; 70 mmol) under reflux conditions (24 hours). The solvent is evaporated to yield the title compound, which is used as such in the next step.

(E) (Z)-1-(4-methylthiobenzylidene)-5-dimethylamino-2-methyl-3-indenyl-(2-hydroxy)ethane Lithium borohydride (1.38 mmol) in THF (2 ml) is added to the suspension of (Z)-1-(4-methylthiobenzylidene)-5-dimethylamino-2-methyl-3-indenylacetyl chloride (2.78 mmol) in THF (20 ml) at 0° C. The reaction is quenched after 5 minutes with HCl (10%, aqueous, 30 ml). Ethyl acetate (50 ml) is added to extract the product.

The organic layer is washed with water (2×50 ml), is dried ($Na_2SO_4$) and is evaporated. The residue containing the title compound is purified with flash chromatography (ethylacetate:hexane 8:2) ($R_1=(CH_3)_2N$, $R_2=CH_3$, $R_3=H$, $R_4=H$, n=1, Y=4-methylthiophenyl, $R_5$ and $R_6$ form a double bond, $R_7=H$, m=1, p=1).

EXAMPLE 4

(Z)-5-Methoxy-2-Methyl-1-(4-Methylthiobenzylidene)-1H-3-Indenyl-(2-Hydroxy) Ethane (A) α-Methyl-β-(p-methoxyphenyl)propionic acid A solution of sodium (2.3 g; 0.1 mol) in absolute alcohol (100 ml), diethyl methylmalonate (17.4 g; 0.1 mol) and p-methoxybenzylchloride (17.3 g; 0.1 mol) is heated at reflux in a water bath for 3 hours, and is poured into water. The aqueous solution is extracted with ether (6×7 ml), and the extracts are dried and evaporated. The crude product containing diethyl methyl-p-methoxybenzyl malonate is saponified by heating with excess 4% sodium hydroxide in aqueous ethanolic solution. The resulting solution is concentrated, is extracted with ether to remove any neutral material, and is acidified with dilute sulfuric acid. The acidic mixture is heated on a steam bath for one hour, is cooled and is extracted with ether. Evaporation of the ether solution gives α-methyl-β(p-methoxy)phenyl propionic acid.

(B) 6-Methoxy-2-methylindanone

α-Methyl-β-(p-methoxy)phenyl propionic acid (15 g) is added to polyphosphoric acid (170 g) at 50° C., and the mixture is heated at 83–90° C. for 2 hours. The syrup is stirred for one-half hour in ice water, is extracted with ether three times. The ether solution is washed with water twice and with 5% $NaHCO_3$ five times until all the acidic material has been removed, and is dried over sodium sulfate. Evaporation of the solution gives the indanone as a pale yellow oil.

(C) Methyl 5-methoxy-2-methyl-3-indenylacetate

A solution of 6-methoxy-2-methylindanone (13.4 g) and methyl bromoacetate (19.3 g) in benzene is added over a period of 5 minutes to 21 g of zinc amalgam (prepared according to Org. Syn. Coll., Vol. 3) in benzene (110 ml) and dry ether (40 ml). A few crystals of iodine are added to start the reaction, and the reaction mixture is maintained at reflux temperature (ca. 65° C.) with external heating. At three-hour intervals, two batches of zinc amalgam (10 g) and bromoester (10 g) are added, and the mixture is then refluxed for 8 hours. After addition of ethanol (30 ml) and acetic acid (150 ml), the mixture is poured into 50% aqueous acetic acid (700 ml). The organic layer is separated, and the aqueous layer is extracted twice with ether. The combined organic layers are washed thoroughly with water, ammonium hydroxide and water, are dried over sodium sulfate, and are evaporated in vacuo, followed by pumping at 80° C. bath temperature (1–2 mm Hg). The residue is crude methyl (1-hydroxy-2-methyl-6-methoxy-indanyl)acetate.

A mixture of the above crude hydroxyester, p-toluenesulfonic acid (20 g) monohydrate and anhydrous calcium chloride (20 g) in toluene (250 ml) is refluxed overnight, and is filtered. The solid residue is washed with toluene. The combined toluene solution is washed with water, sodium bicarbonate, and water; and is dried over sodium sulfate. After evaporation, the residue containing methyl 5-methoxy-2-methyl-3-indenylacetate is chromatographed on acid-washed alumina, and is eluted with ether hexanes (2:1).

(D) (Z)-5-Methoxy-2-methyl-1-(p-methylthiobenzylidene)-3-indenylacetic acid

A mixture of 25% methanolic sodium methoxide (16 ml, 2 equivalent), methyl 5-methoxy-2-methyl-3-indenylacetate (8.7 g; 0.037 mol) and p-methylthiobenzaldehyde (6.3 g; 1.1 equivalent) is stirred at reflux under nitrogen for 2 hours. An equal volume of water is added dropwise and heating is continued for 30 min. The solution is cooled, is diluted with water and is extracted with ether. The aqueous solution is freed from ether by bubbling with nitrogen, and is acidified with 10% hydrochloric acid. The precipitate is collected, is washed thoroughly with water, and is crystallized from methanol to give pure (Z)-5-methoxy-2-methyl-1-(p-methylthiobenzaldehyde)-3-indenylacetic acid (m.p. 195–196° C.).

(E) (Z)-5-Methoxy-2-methyl-1-(4-methylthiobenzylidene)-3-indenylacetyl chloride (Z)-5-methoxy-2-methyl-1-(p-methylthiobenzylidene)-3-indenylacetic acid (70 mmol) in absolute THF (500 ml) is heated with oxalylchloride (2 M in $CH_2Cl_2$; 70 mmol) at reflux (24 hours). The solvent is evaporated to yield the title compound, which is used as such in the next step.

(F) (Z)-5-Methoxy-2-methyl-1-(4-methylthiobenzylidene)-1H-3-indenyl-(2-hydroxy)ethane Lithium borohydride (1.38 mmol) in THF (2 ml) is added slowly to a solution of (Z)-5-methoxy-2-methyl-1-(4-methylthiobenzylidene)-3-indenylacetyl chloride (2.78 mmol) in THF (20 ml) at 0° C. The reaction is quenched after 5 minutes with HCl (10%, aqueous, 30 ml). Ethyl acetate (50 ml) is added to extract the product.

The organic layer is washed with water (2×50 ml), is dried ($Na_2SO_4$) and is evaporated. The residue which contains the title compound is subjected to flash chromatography (ethylacetate:hexane, 8:2, $SiO_2$) ($R_1=CH_3O$, $R_2=CH_3$, $R_3=H$, $R_4=H$, Y=4-methylthiophenyl, n=1, $R_5$ and $R_6$ form a double bond, $R_7=H$, m=1, p=1).

EXAMPLE 5

(Z)-6-Fluoro-5-Methoxy-2-Methyl-1-(4-Methylthiobenzylidene)-1H-3-Indenyl-(2-Hydroxy) Ethane (A) 3-Fluoro-4-methoxybenzaldehyde A solution of titanium tetrachloride (182 g, 0.96 mol, 1.2 equiv.) and α,α,-dichloromethylmethyl ether (110 g, 0.96 mol) in an equal volume of methylene chloride is slowly added (30 minutes) to a solution of o-fluoroanisole (101 g, 0.80 mol) in dry methylene chloride (50 ml) at 10–20° C. The mixture is stirred at room temperature for one hour, is poured over crushed ice water and ether (1 1) with stirring. This mixture is stirred under nitrogen until solution occurs. The organic layer is extracted with water, aqueous sodium bicarbonate, and is dried ($MgSO_4$). The solvent is evaporated at 30° C. The residual oil is vacuum-distilled through a jacketed Vigreux column to give 3-fluoro-4-methoxybenzaldehyde, B.P. 120–121° C. (10 mm Hg) $R_f$ 0.6 on a silica-gel G plate with methylene chloride.

(B) 3-Fluoro-4-methoxy-α-methylcinnamic acid

A mixture of 3-fluoro-4-methoxybenzaldehyde (34.2 g, 0.22 mol), propionic anhydride (50 g, 0.38 mol) and sodium propionate (21 g, 0.22 mol) is stirred under nitrogen at 150° C. for 15 hours, and is poured into water (1.3 l). The precipitate is filtered off, and is dissolved in 2.0 N potassium hydroxide solution (500 ml) with stirring for several hours.

The aqueous solution is washed with ether, and is acidified with concentrated hydrochloric acid. The precipitate is collected, is washed thoroughly with water, and is dried in a vacuum oven at 50° C. over potassium hydroxide pellets to give 3-fluoro-α-methyl-4-methoxycinnamic acid, m.p. 167–169° C.; $R_f$ 0.5 (silica-gel G with methylene chloride-methanol, 1:1).

(C) 3-Fluoro-4-methoxy-α-methyl dihydrocinnamic acid

3-Fluoro-4-methoxy-α-methylcinnamic acid (49.5 g, 0.236 mol) in methanol (800 ml) at 20° C. is hydrogenated at 43 psi until the theoretical uptake of hydrogen has occurred (24 min. with 1.5 g platinum oxide catalyst). The solution is filtered, and is evaporated with warming to 60° C. to give 3-fluoro-4-methoxy-α-methyl dihydrocinnamic acid, $R_f$ 0.5 on silica-gel G with methylene chloride-methanol (9:1).

(D) 5-Fluoro-6-methoxy-2-methylindanone

A mixture of 3-fluoro-α-methyl-4-methoxy dihydrocinnamic acid, (49.3 g, 0.23 mol) in polyphosphoric acid (500 g) is heated at 95° C. on a steam bath with occasional agitation for 75 min. The dark red solution is stirred with water (3.0 l) overnight. The precipitate is collected, and is washed thoroughly with water. Its solution in ether is extracted with aqueous potassium bicarbonate (4×), is diluted with methylene chloride, is dried ($MgSO_4$), and is evaporated. The residue is recrystallized from methylene chloride/hexanes to give 5-fluoro-6-methoxy-2-methylindanone (m.p. 76–78°).

(E) Methyl 6-fluoro–5-methoxy-2-methyl-3-indenyl-acetate

A zinc sheet (6.0 g) in dry benzene (100 ml) is placed into a 500 ml three-necked flask, fitted with mechanical stirrer, reflux condenser, drying tube, dropping funnel and nitrogen inlet. A few milliliters of a solution of 5-fluoro-6-methoxy-2-methylindanone (21.3 g, 0.11 mol) and methyl bromoacetate (18.36 g, 0.121 mol) in dry benzene (100 ml) is added. A crystal of iodine is added. The mixture is gently heated with stirring. After the iodine color has disappeared, the remainder of the mixture is added gradually. The mixture is heated at reflux for 18 hours, and is poured onto 5% aqueous $H_2SO_4$ (600 ml), and ice (500 g). Ether is added; and the organic layer is washed with three portions each of 5% aqueous $H_2SO_4$, aqueous $KHCO_3$, and water, is dried ($MgSO_4$), and is concentrated to give a reddish oil (27.6 g) which crystallizes slowly. Thin-layer chromatography on silicagel G with methylene chloride methanol (99:1) shows a strong spot at $R_f$ 0.5.

The oil is stirred and heated at reflux with phosphorus pentoxide for one-half hour. The mixture is cooled, and is filtered. The filtercake is triturated with benzene. The benzene extracts are washed with two portions of salt water, are dried ($MgSO_4$), and are concentrated, to give a slightly colored oil which rapidly crystallizes. The crystals are recrystallized from methylene chloride-hexanes to give methyl 6-fluoro-5-methoxy-2-methyl-3-indenyl-acetate (m.p. 61–62° C.).

(F) (Z)-6-Fluoro-5-methoxy-2-methyl-1-(p-methylthiobenzylidene)-3-indenylacetic acid A mixture of methyl 6-fluoro-5-methoxy-2-methyl-3-indenyl acetate (9.3 g (0.037 mol), p-methylthiobenzaldehyde (6.3 g, 1.1 equivalent) and 25% methanolic sodium methoxide (16 ml, 2.0 equivalents) is stirred at reflux under nitrogen for 2 hours. An equal volume of water is added dropwise, and reflux is continued for 30 minutes. The solution is diluted with water, and is washed with ether. Residual ether is removed by bubbling with nitrogen. The aqueous solution is acidified with 50% aqueous acetic acid. The precipitate is collected, is washed thoroughly with water and is recrystallized from methanol to give (Z)-6-fluoro-5-methoxy-2-methyl-1-(p-methylthiobenzylidene)-2-indenylacetic acid, m.p. 172–174° C.

(G) (Z)-6-Fluoro-5-methoxy-2-methyl-1-(4-methylthiobenzylidene)-3-indenylacetyl chloride (Z)-6-fluoro-5-methoxy-2-methyl-1-(p-methylthiobenzylidene)-2-indenylacetic acid (70 mmol) in THF (500 ml) is allowed to react with oxalylchloride (2 M in $CH_2Cl_2$; 35 ml, 70 mmol) under reflux conditions (24 hours). The solvent is evaporated to yield the title compound as a residue, which is used as such in the next step.

(I) (Z)-6-Fluoro-5-methoxy-2-methyl-1-(4-methylthiobenzylidene)-1H-3-indenyl-(2-hydroxy)ethane Lithium borohydride (1.38 mmol) in THF (2 ml) is added to the solution of (Z)-5-fluoro-2-methyl-1-(4-methylthiobenzylidene)-3-indenylacetyl chloride (2.78 mmol) in THF (20 ml) at 0° C. The reaction is quenched after 5 minutes with HCl (10%, aqueous, 30 ml). The product is extracted with ethyl acetate (50 ml).

The organic layer is washed with water (2×50 ml), is dried over $Na_2SO_4$ and is evaporated. The residue, which contains the title compound, is purified with flash chromatography (ethylacetate:hexane 8:2) ($R_1$=F, $CH_3O$; $R_2$=$CH_3$; $R_3$=H; $R_4$=H; Y=4-methylthiophenyl, n=2, $R_5$ and $R_6$ form a double bond, $R_7$=H, m=1, p=1).

EXAMPLE 6

(Z)-5-Methoxy-2-Methyl-1-Benzylidene-1H-3-Indenyl-(2-Hydroxy)Ethane (A) (Z)-5-Methoxy-2-methyl-1-benzylidene-3-indenylacetic acid.

(Z)-5-methoxy-2-methyl-1-benzylidene-3-indenylacetic acid is obtained, if methyl 5-methoxy-2-methyl-3-indenylacetate (see Example 4, Part C) is allowed to react with benzaldehyde according to the procedure of Example 4, Part D.

(B) (Z)-5-Methoxy-2-methyl-1-benzylidene-3-indenylacetyl chloride (Z)-5-methoxy-2-methyl-1-benzylidene-3-indenylacetic acid (70 mmol) in THF (500 ml) is allowed to react with oxalylchloride (2 M in $CH_2Cl_2$; 70 mmol) under reflux conditions (24 hours). The solvent is evaporated to yield the title compound, which is used as such in the next step.

(C) (Z)-5-methoxy-2-methyl-1-benzylidene-1H-3-indenylacetic-(2-hydroxy)ethane

Lithium borohydride (1.38 mmol) in THF (2 ml) is allowed to react with (Z)-5-methoxy-2-methyl-1-benzylidene-3-indenylacetyl chloride (2.78 mmol) in THF (20 ml) at 0° C. The reaction is quenched after 5 minutes with 10% aqueous HCl (30 ml), ethyl acetate (50 ml) is added to extract the product.

The organic layer is washed with water (2×50 ml), is dried over $Na_2SO_4$ and is evaporated. The residue, which contains the title compound, is purified with flash chromatography (ethylacetate:hexane 8:2)($R_1$=$CH_3O$, $R_2$=$CH_3$, $R_3$=H, $R_4$=H, Y=phenyl, n=1, $R_5$ and $R_6$ form a double bond, $R_7$=H, m=1, p=1).

EXAMPLE 7

(Z)-5-Methoxy-2-Methyl-1-Chlorobenzylidene-1H-3-Indenyl-(2-Hydroxy)Ethane (A) (Z)-5-Methoxy-2-methyl-1-(p-chlorobenzylidene)-3-indenylacetic acid (Z)-5-Methoxy-2-methyl-1-chlorobenzylidene-3-indenylacetic acid is obtained, if methyl 5-methoxy-2-methyl-3-indenylacetate (see Example 4, Part C) is allowed to react with p-chlorobenzaldehyde according to the procedure of Example 4, Part D.

(B) (Z)-5-Methoxy-2-methyl-1-chlorobenzylidene-3-indenylacetyl chloride (Z)-5-Methoxy-2-methyl-1-chlorobenzylidene-3-indenylacetic acid (70 mmol) in THF (500 ml) is allowed to react with oxalylchloride (2 M in $CH_2Cl_2$; 70 mmol) under reflux conditions (24 hours). The solvent is evaporated to yield the title compound, which is used as such in the next step.

(C) (Z)-5-Methoxy-2-methyl-1-(4-chlorobenzylidene)-1H-3-indenyl-(2-hydroxy)ethane Lithium borohydride (1.38 mmol) in THF (2 ml) is added to the solution of (Z)-5-Methoxy-2-methyl-1-chlorobenzylidene-3-indenylacetyl chloride (2.78 mmol) in THF (20 ml) at 0° C. The reaction is quenched with 10%, aqueous HCl (30 ml). After 5 minutes, ethyl acetate (50 ml) is added in order to extract the product.

The organic layer is washed with water (2×50 ml), is dried ($Na_2SO_4$), and is evaporated. The residue is purified by flash chromatography to give the title compound (ethylacetate:hexane 8:2)($R_1$=$CH_3O$, $R_2$=$CH_3$, $R_3$=H, $R_4$=H, Y=4-chlorophenyl, n=1, $R_5$ and $R_6$ form a double bond, $R_7$=H, m=1, p=1).

EXAMPLE 8

(Z)-5-Fluoro-2-Methyl-1-(3,4,5-Trimethoxybenzylidene)-1H-3-Indenyl-(2-Hydroxy)Ethane (A) (Z)-5-Fluoro-2-methyl-1-(3,4,5-trimethoxybenzylidene)-3-acetic acid When 5-fluoro-2-methylindene-3-acetic acid (see Example 1, Part D) is allowed to react with 3,4,5-trimethoxybenzaldehyde according to the procedure of Example 1, (part E) the title compound, (Z)-5-fluoro-2-methyl-1-(3,4,5-trimethoxybenzylidene)-3-indenylacetic acetic acid, is obtained. $C_{22}H_{21}FO_5$: 384.40; m.p. 168° C.

(B) (Z)-5-Fluoro-2-methyl-1-(3,4,5-trimethoxybenzylidene)-3-indenylacetyl chloride (Z)-5-fluoro-2-methyl-1-(3,4,5-trimethoxybenzylidene)-3-acetic acid (70 mmol) in THF (500 ml) is allowed to react with oxalylchloride (2 M in $CH_2Cl_2$; 35 ml, 70 mmol) under reflux conditions (24 hours). The solvent is evaporated to yield the title compound, which is used as such in the next step.

(C) (Z)-5-fluoro-2-methyl-1-(3,4,5-trimethoxybenzylidene)-1H-3-indenyl-(2-hydroxy)ethane Lithium borohydride (1.38 mmol) in THF (2 ml) is added to a suspension of (Z)-5-Fluoro-2-methyl-1-(3,4,5-trimethoxybenzylidene)-3-indenylacetyl chloride (2.78 mmol) in THF (20 ml) at 0° C. The reaction is quenched after 5 minutes with HCl (10%, aqueous, 30 ml). Ethyl acetate (50 ml) is added in order to extract the product. The organic layer is washed with water (2×50 ml), is dried over $Na_2SO_4$ and is evaporated to give the title compound, which is purified with flash chromatography (ethylacetate:hexane 8:2). ($R_1$=F, $R_2$=$CH_3$, $R_3$=H, $R_4$=H, Y=3,4,5-trimethoxyphenyl, n=1, $R_5$ and $R_6$ form a double bond, $R_7$=H, m=1, p=1).

$^1$H-NMR ($CDCl_3$) 7.43 (m, 1H, ar), 7.12 (s, 1H, =CH), 6.87 (m,1H, ar), 6.75 (s, 2H, ar), 6.60 (m, 1H, ar),3.93 (s, 3H, $OCH_3$), 3.85 (s, 6H, $OCH_3$), 3.86 (t, 2H, $CH_2OH$), 2.85 (t, 2H, $CH_2$), 2.20 (s, 3H, $CH_3$).

EXAMPLE 9

(Z)-5-Fluoro-2-Methyl-1-(4-Methylsulfonylbenzylidene)-1H-3-Indenyl-(2-Hydroxy)Ethane (A) Methyl 5-fluoro-2-methyl1-3-indenylacetate Nitrosomethylurea (99.5 mmol) is added in portions to a cold (0° C.) mixture of aqueous 50% KOH (50 ml) and diethylether (150 ml) at 0° C. The yellow ether solution of diazomethane (Note: explosive) is separated, is washed with water, and is added in portions to a solution of 5-fluoro-2-methylindenyl-3-acetic acid (90 mmol) (Example 1D) in dichloromethane (200 ml). When the evolution of $N_2$ ceases, the reaction is complete. After evaporation of the solvents, the residue is recrystallized from hexane to give methyl 5-fluoro-2-methyl-3-indenylacetate (yield 93%; m.p. 53° C.).

(B) 5-Fluoro-2-methyl-1H-3-indenyl-(2-hydroxy)ethane

To a solution of methyl 5-fluoro-2-methyl-3-indenylacetate (24 g) in dry THF (300 ml) lithiumaluminum hydride (6.9 g) is added. The mixture is stirred at room temperature for 1.5 hours. Excess LiAlH$_4$ is destroyed with saturated aqueous NaHSO$_4$ solution. The organic phase is concentrated in vacuo, and the crude product is purified via silica gel column chromatography elution with methylene chloride. The residue is recrystallized from hexane to give 5-fluoro-2-methyl-1H-3-indenyl-(2-hydroxy)ethane (yield 63%; m.p. 65°–66.5° C.).

(C) (Z)-5-Fluoro-2-Methyl-1-(4-Methylsulfonylbenzylidene)-1H-3-Indenyl-(2-Hydroxy)Ethane 5-Fluoro-2-methyl-1H-3-indenyl-(2-hydroxy)ethane (15 g, 0.072 mol) p-methylsulfonylbenzaldehyde (14.0 g, 0.091 mol) and sodium methoxide (13.0 g, 0.24 mol) are heated in methanol (200 ml) at 60° C. under nitrogen with stirring for 6 hours. The reaction mixture is poured onto ice-water (750 g), and is acidified with 2.5N hydrochloric acid. The collected solid is triturated with a little ether to produce (Z)-5-fluoro-2-methyl-1-(p-methylsulfonylbenzylidene)-1H-3-indenyl-(2-hydroxy)ethane. Recrystallization of the crude reaction product results in the separation of the mixture of geometrical isomers (Z/E) and gives the title compound ($R_1$=F, $R_2$=CH$_3$, $R_3$=H, $R_4$=H, Y=4-methylsulfonylphenyl, n=1, $R_5$ and $R_6$ form a double bond, $R_7$=H, m=1, p=1).

Formula: $C_{20}H_{19}FO_3S$.

Molecular Mass: 358.43 g/mol.

Melting point: 118° C.

$^1$H-NMR [ppm] (DMSO-d$_6$): 2.14 (s,3,—CH$_3$); 2.71 (t,2,—CH$_2$—); 3.29 (s,3,—SO$_3$—CH$_3$); 3.55 (m,3,—CH$_2$—O); 4.70 (m,1,—OH); 6.68–7.14 (m,3,ar.);7.30 (s,1,=CH); 7.76–8.03 (AB,4,—Ph—SO$_2$—).

IR [cm$^{-1}$] (KBr): 3440 OH; 1300 S=O; 1170 C—F; 1140 S=O.

EXAMPLE 10

(Z)-5-Fluoro-2-Methyl-1-(4-Pyridinylidene)-1H-3-Indenyl-(2-Hydroxy)Ethane

Following the procedure of Example 9, part C, 4-pyridinecarboxaldehyde is used instead of p-methylsulfonylbenzaldehyde in the base-catalyzed condensation to obtain the title compound after recrystallization of the Z/E mixture. ($R_1$=F; $R_2$ =CH$_3$; $R_3$=H; $R_4$=H; Y=4-pyridinyl; m, n, p=1; $R_5$, $R_6$ form a double bond; $R_7$=H).

EXAMPLE 11

(Z)-5-Fluoro-2-Methyl-1-(3-Pyridinylidene)-1H-3-Indenyl-(2-Hydroxy)Ethane

Following the procedure of Example 9, part C, 3-pyridinecarboxaldehyde is used instead of p-methylsulfonylbenzaldehyde in the base-catalyzed condensation, to yield the title compound after recrystallization of the Z/E mixture. ($R_1$=F; $R_2$=CH$_3$; $R_3$=H; $R_4$=H; Y=3-pyridinyl; m, n, p=1; $R_5$, $R_6$ form a double bond; $R_7$=H).

EXAMPLE 12

(Z)-5-Fluoro-2-Methyl-1-(2-Pyridinylidene)-1H-3-Indenyl-(2-Hydroxy)Ethane

Following the procedure of Example 9, part C, 2-pyridinecarboxaldehyde is used instead of p-methylsulfonylbenzaldehyde in the base-catalyzed condensation to yield the title compound after recrystallization of the Z/E mixture. ($R_1$=F; $R_2$=CH$_3$; $R_3$=H; $R_4$=H; Y=2-pyridinyl; m, n, p=1; $R_5$, $R_6$ form a double bond; $R_7$=H).

EXAMPLE 13

(Z)-5-Fluoro-2-Methyl-1-(4-Quinolinylidene)-1H-3-Indenyl-(2-Hydroxy)Ethane

Following the procedure of Example 9, part C, 4-quinolinecarboxaldehyde is used instead of p-methylsulfonylbenzaldehyde in the base-catalyzed condensation to obtain the title compound after recrystallization of the Z/E mixture. ($R_1$=F; $R_2$=CH$_3$; $R_3$=H; $R_4$=H; Y=4-quinolinyl; m, n, p=1; $R_5$, $R_6$ form a double bond; $R_7$=H).

EXAMPLE 14

(Z)-5-Fluoro-2-Methyl-1-(4,6 Dimethyl-2-Pyridinylidene)-1H-3-Indenyl-(2-Hydroxy)Ethane Following the procedure of Example 9, part C, 4,6-dimethyl-2-pyridinecarboxaldehyde is used instead of p-methylsulfonylbenzaldehyde in the base-catalyzed condensation to obtain the title compound after recrystallization of the Z/E mixture. ($R_1$=F; $R_2$=CH$_3$; $R_3$=H; $R_4$=H; Y=4,6-dimethyl-2-pyridinyl; m, n, p=1; $R_5$, $R_6$ form a double bond; $R_7$=H).

EXAMPLE 15

(Z)-5-Fluoro-2-Methyl-1-(3-Quinolinylidene)-1H-3-Indenyl-(2-Hydroxy)Ethane

Following the procedure of Example 9, part C, 3-quinolinecarboxaldehyde is used instead of p-methylsulfonylbenzaldehyde in the base-catalyzed condensation, to yield the title compound after recrystallization of the Z/E mixture. ($R_1$=F; $R_2$=CH$_3$; $R_3$=H; $R_4$=H; Y=3-quinolinyl; m, n, p=1; $R_5$, $R_6$ form a double bond; $R_7$=H).

EXAMPLE 16

(Z)-5-Fluoro-2-Methyl-1-(2-Quinolinylidene)-1H-3-Indenyl-(2-Hydroxy)Ethane

Following the procedure of Example 9, part C, 2-quinolinecarboxaldehyde is used instead of p-methylsulfonylbenzaldehyde in the base-catalyzed condensation to obtain the title compound after recrystallization of the Z/E mixture. ($R_1$=F; $R_2$=CH$_3$; $R_3$=H; $R_4$=H; Y=2-quinolinyl; m, n, p=1; $R_5$, $R_6$ form a double bond; $R_7$=H).

EXAMPLE 17

(Z)-5-Fluoro-2-Methyl-1-(1-Pyrazinylidene)-1H-3-Indenyl-(2-Hydroxy)Ethane

Following the procedure of Example 9, part C, pyrazine-1-aldehyde (prepared according to Rutner et al. JOC 1963, 28, 1898–99) is used instead of p-methylsulfonylbenzaldehyde in the base-catalyzed condensation to yield the title compound after recrystallization of the Z/E mixture. ($R_1$=F; $R_2$=CH$_3$; $R_3$=H; $R_4$=H; Y=pyrazinyl; m, n, p=1; $R_5$, $R_6$ form a double bond; $R_7$=H).

EXAMPLE 18

(Z)-5-Fluoro-2-Methyl-1-(3-Pyridazinylidene)-1H-3-Indenyl-(2-Hydroxy)Ethane

Following the procedure of Example 9, part C, pyridazine-3-aldehyde (prepared according to Heinisch et al., Monatshefte f. Chem., 108, 213–224, 1977) is used instead of p-methylsulfonylbenzaldehyde in the base-catalyzed condensation to yield the title compound after recrystallization of the Z/E mixture. ($R_1$=F; $R_2$=$CH_3$; $R_3$=H; $R_4$=H; Y=3-pyridazinyl; m, n, p=1; $R_5$, $R_6$ form a double bond; $R_7$=H).

EXAMPLE 19

(Z)-5-Fluoro-2-Methyl-1-(4-Pyrimidinylidene)-1H-3-Indenyl-(2-Hydroxy)Ethane

Following the procedure of Example 9, part C, pyrimidine-4-aldehyde (prepared according to Bredereck et al., Chem. Ber. 1964, 97, 3407–17) is used instead of p-methylsulfonylbenzaldhyde in the base-catalyzed condensation. The title compound is obtained after recrystallization of the Z/E mixture. ($R_1$=F; $R_2$=$CH_3$; $R_3$=H; $R_4$=H; Y=pyrimidinyl; m, n, p=1; $R_5$, $R_6$ form a double bond; $R_7$=H).

EXAMPLE 20

(Z)-5-Fluoro-2-Methyl-1-(2-Methyl-4-Pyrimidinylidene)-1H-3-Indenyl-(2-Hydroxy)Ethane Following the procedure of Example 9, part C, 2-methylpyrimidine-4-aldehyde (prepared according to Bredereck et al., Chem. Ber. 1964, 97, 3407–17) is used instead of p-methylsulfonylbenzaldehyde in the base-catalyzed condensation, the title compound is obtained after recrystallization of the Z/E mixture. ($R_1$=F; $R_2$=$CH_3$; $R_3$=H; $R_4$=H; Y=2-methyl-4-pyrimidinyl; m, n, p=1; $R_5$, $R_6$ form a double bond; $R_7$=H).

EXAMPLE 21

(Z)-5-Fluoro-2-Methyl-1-(4-Pyridazinylidene)-1H-3-Indenyl-(2-Hydroxy)Ethane

Following the procedure of Example 9, part C, pyridazine-4-carboxaldehyde (prepared according to Heinisch et al., Monatshefte f. Chem., 104, 1372–1382, 1973) is used instead of p-methylsulfonylbenzylaldehyde in the base-catalyzed condensation to obtain the title compound after recrystallization of the Z/E mixture. ($R_1$=F; $R_2$=$CH_3$; $R_3$=H; $R_4$=H; Y=pyridazinyl; m, n, p=1; $R_5$, $R_6$ form a double bond; $R_7$=H).

EXAMPLE 22

(Z)-5-Fluoro-2-Methyl-1-(1-Methyl-3-Indolylidene)-1H-3-Indenyl-(2-Hydroxy)Ethane Following the procedure of Example 9, part C, 1-methylindole-3-carboxaldehyde is used instead of p-methylsulfonylbenzaldehyde in the base-catalyzed condensation to produce the title compound after recrystallization of the Z/E mixture. ($R_1$=F; $R_2$=$CH_3$; $R_3$=H; $R_4$=H; Y=1-methyl-3-indolyl; m, n, p=1; $R_5$, $R_6$ form a double bond; $R_7$=H).

EXAMPLE 23

(Z)-5-Fluoro-2-Methyl-1-(1-Acetyl-3-Indolylidene)-1H-3-Indenyl-(2-Hydroxy)Ethane Following the procedure of Example 9, part C, 1-acetyl-3-indolecarboxaldehyde is used instead of p-methylsulfonylbenzaldehyde in the base-catalyzed condensation to obtain the title compound after recrystallization of the Z/E mixture. ($R_1$=F; $R_2$=$CH_3$; $R_3$=H; $R_4$=H; Y=1-acetyl-3-indolyl; m, n, p=1; $R_5$, $R_6$ form a double bond; $R_7$=H).

EXAMPLE 24

(Z)-5-Fluoro-2-Methyl-1-(2-Pyrrolylidene)-1H-3-Indenyl-(2-Hydroxy)Ethane

Following the procedure of Example 9, part C, pyrrol-2-aldehyde is used instead of p-methylsulfonylbenzaldehyde in the base-catalyzed condensation, the title compound is obtained after recrystallization of the Z/E mixture. ($R_1$=F; $R_2$=$CH_3$; $R_3$=H; $R_4$=H; Y=2-pyrrolyl; m, n, p=1; $R_5$, $R_6$ form a double bond; $R_7$=H).

EXAMPLE 25

(Z)-5-Fluoro-2-Methyl-1-(2-Pyrimidinylidene)-1H-3-Indenyl-(2-Hydroxy)Ethane

Following the procedure of Example 9, part C, pyrimidine-2-aldehyde is used instead of p-methylsulfonylbenzaldehyde in the base-catalyzed condensation to yield the title compound after recrystallization of the Z/E mixture. ($R_1$=F; $R_2$=$CH_3$; $R_3$=H; $R_4$=H; Y=2-pyrimidinyl; m, n, p=1; $R_5$, $R_6$ form a double bond; $R_7$=H).

EXAMPLE 26

(Z)-5-Fluoro-2-Methyl-1-[2-(1-Methyl)Benzimidazolylidene]-1H-3-Indenyl-(2-Hydroxy)Ethane Following the procedure of Example 9, part C, using 2-(1-methyl)benzimidazole-2-aldehyde is used instead of p-methylsulfonylbenzaldehyde in the base-catalyzed condensation to obtain the title compound after recrystallization of the Z/E mixture. ($R_1$=F; $R_2$=$CH_3$; $R_3$=H; $R_4$=H; Y=2-(1-methyl)benzimidazolyl; m, n, p=1; $R_5$, $R_6$ form a double bond; $R_7$=H).

EXAMPLE 27

(Z)-5-Fluoro-2-Methyl-1-[2-(6-Methyl)Pyridinylidene]-1H-3-Indenyl-(2-Hydroxy)Ethane Following the procedure of Example 9, part C, 6-methylpyridine-2-aldehyde is used instead of p-methylsulfonylbenzaldehyde in the base-catalyzed condensation, to produce the title compound after recrystallization of the Z/E mixture. ($R_1$=F; $R_2$=$CH_3$; $R_3$=H; $R_4$=H; Y=2-(6-methyl)pyridinyl; m, n, p=1; $R_5$, $R_6$ form a bond; $R_7$=H).

EXAMPLE 28

(Z)-5-Fluoro-2-Methyl-1-(4-Isoquinolinylidene)-1H-3-Indenyl-(2-Hydroxy)Ethane

Following the procedure of Example 9, part C, isoquinoline-4-aldehyde is used instead of p-methylsulfonylbenzaldehyde in the base-catalyzed condensation to obtain the title compound after recrystallization of the Z/E mixture. ($R_1$=F; $R_2$=$CH_3$; $R_3$=H; $R_4$=H; Y=4-isoquinolinyl; m, n, p=1; $R_5$, $R_6$ form a double bond; $R_7$=H).

EXAMPLE 29

(Z)-5,6-Difluoro-2-Methyl-1-(4-Methylsulfonylbenzylidene)-1H-3-Indenyl-(2-Hydroxy)Ethane (A) (Z)-5,6-Difluoro-2-methyl-1-(p-methylsulfonylbenzylidene)-indene-3-acetic acid Methyl 5,6-difluoro-2-methylindene-3-acetate (1.19 g, 5.0 mmol) from Example 2, Part E and of p-methylsulfonylbenzaldehyde (0.76 g, 5.0 mmol) in dry pyridine (10 ml) are treated under nitrogen with Triton B (5.0 g, 5.1 mmol). The deeply colored solution is kept overnight. Water (2 ml) is added, the solution is stirred for 15 minutes and is poured into excess water. The mixture is extracted with ether (2×50 ml). The aqueous phase is added to 10% HCl-ice. The solution of the precipitate is extracted into methylene chloride and is dried ($MgSO_4$). The solvent is evaporated to leave an orange solid which is recrystallized from benzene to give (Z)-5,6-difluoro-2-methyl-1-(p-methylsulfonylbenzylidene)-indene-3-acetic acid.

(B) (Z)-5,6-Difluoro-2-methyl-1-(4-methylsulfonylbenzylidene)-3-indenylacetyl chloride The title compound is obtained according to the procedure of Example 1, Part F.

(C) (Z)-5,6-Difluoro-2-methyl-1-(4-methylsulfonylbenzylidene)-1H-3-indenyl-(2-hydroxy)ethane The title compound is obtained according to the procedure of Example 1, Part G. ($R_1$=5,6 difluoro; $R_2$=$CH_3$; $R_3$=H; $R_4$=H; n=2; Y=4-methylsulfonyphenyl, $R_5$ and $R_6$ form a double bond, $R_7$=H, m=1, p=1)

EXAMPLE 30

(Z)-1-(4-Methylsulfonylbenzylidene)-5-Dimethylamino-2-Methyl-1H-3-Indenyl-(2-Hydroxy)Ethane (A) (Z) 1-(p-Methylsulfonylbenzylidene)-5-dimethylamino-2-methyl-3-indenyl acetic acid p-Methylsulfonylbenzaldehyde (1.5 g) is added to a solution of methyl 5-dimethylamino-2-methyl-3-indenylacetate (2.5 g) from Example 3 Part B in 1,2-dimethoxyethane (1.5 ml) at 0° C. followed by the addition of potassium t-butoxide (1.1 g). The reaction mixture is kept in the ice-bath for 4 hours and at room temperature for 18 hours. The mixture is diluted with ether (15 ml), and the potassium salt is filtered off. The salt is dissolved in 30 ml of water and neutralized with dilute hydrochloric acid to pH 6–6.5. The crude acid precipitates, is collected by filtration and is recrystallized to give pure (Z)-1-(p-methylsulfonylbenzylidene)-5-dimethylamino-2-methyl-3-indenylacetic acid.

(B) (Z)-1-(4-Methylsulfonylbenzylidene)-5-dimethylamino-2-methyl-3-indenylacetyl chloride (Z)-1-(p-methylsulfonylbenzylidene)-5-dimethylamino-2-methyl-3-indenylacetic acid (70 mmol) in THF (500 ml) is allowed to react with oxalylchloride (2 M in $CH_2Cl_2$; 70 mmol) under reflux conditions (24 hours). The solvent is evaporated to yield the title compound, which is used as such in the next step.

(C) (Z)-1-(4-methylsulfonylbenzylidene)-5-dimethylamino-2-methyl-1H-3-indenyl-(2-hydroxy)ethane Lithium borohydride (1.38 mmol) in THF (2 ml) is added to the solution of (Z)-1-(4-methylsulfonylbenzylidene)-5-dimethylamino-2-methyl-3-indenylacetyl chloride (2.78 mmol) in THF (20 ml) at 0° C. The reaction is quenched with HCl after 5 minutes (10%, aqueous, 30 ml). Ethyl acetate (50 ml) is added to extract the product.

The organic extract is washed with water (2×50 ml), is dried over $Na_2SO_4$ and is concentrated. The residue containing the title compound is purified by flash chromatography (ethylacetate:hexane 8:2) ($R_1$=$(CH_3)_2$N, $R_2$=$CH_3$, $R_3$=H, $R_4$=H, n=1, Y=4-methylsulfonylphenyl; $R_5$ and $R_6$ form a double bond, $R_7$=H, m=1, p=1).

EXAMPLE 31

(Z)-5-Methoxy-2-Methyl-1-(4-Methylsulfonylbenzylidene)-1H-3-Indenyl-(2-Hydroxy)Ethane (A) (Z)-5-Methoxy-2-methyl-1-(p-methylsulfonylbenzylidene)-3-indenylacetic acid 25% methanolic sodium methoxide (16 ml, 2.0 equivalents) is treated with a solution of methyl 5-methoxy-2-methyl-3-indenylacetate (from Example 4, Part C) (8.7 g; 0.037 mol) and p-methylsulfonylbenzaldehyde, (6.3 g; 1.1 equivalent). The mixture is stirred at reflux under nitrogen for 2 hours. An equal volume of water is added slowly, and refluxing is continued for 30 min. The solution is cooled, is diluted with water and is washed with ether. Residual ether is blown off with nitrogen. The aqueous solution is acidified with 10% hydrochloric acid. The precipitated product is collected and is washed thoroughly with water. The crude product is crystallized from methanol to give (Z)-5-methoxy-2-methyl-1-(p-methylsulfonylbenzylidene)-3-indenylacetic acid.

(B) (Z)-5-Methoxy-2-methyl-1-(4-methylsulfonylbenzylidene)-3-indenylacetyl chloride (Z)-5-methoxy-2-methyl-1-(p-methylsulfonylbenzylidene)-3-indenylacetic acid (70 mmol) in THF (500 ml) is allowed to react with oxalylchloride (2 M in $CH_2Cl_2$; 35 ml) under reflux conditions (24 hours). The solvent is evaporated to yield the title compound, which is used as such in the next step.

(C) (Z)-5-Methoxy-2-methyl-1-(4-methylsulfonylbenzylidene)-1H-3-indenyl-(2-hydroxy)ethane Lithium borohydride (1.38 mmol) in THF (2 ml) is added to a solution of (Z)-5-methoxy-2-methyl-1-(4-methylsulfonylbenzylidene)-3-indenylacetyl chloride (2.78 mmol) in THF (20 ml) at 0° C. The reaction is quenched with HCl (10%, aqueous, 30 ml) after 5 minutes. Ethyl acetate (50 ml) is added to extract the product.

The organic layer is washed with water (2×50 ml), is dried ($Na_2SO_4$) and is concentrated to give the title compound, which is purified by flash chromatography (ethylacetate:hexane 8:2) ($R_1$=$CH_3$O, $R_2$=$CH_3$, $R_3$=H, $R_4$=H, Y=4-methylsulfonylphenyl, n=1, $R_5$ and $R_6$ form a double bond, $R_7$=H, m=1, p=1).

EXAMPLE 32

(Z)-6-Fluoro-5-Methoxy-2-Methyl-1-(4-Methylsulfonylbenzylidene)-1H-3-Indenyl-(2-Hydroxy)Ethane (A) (Z)-6-Fluoro-5-methoxy-2-methyl-1-(p-methylsulfonylbenzylidene)-3-indenylacetic acid 25% methanolic sodium methoxide (16 ml, 2.0 equivalents) is added to a solution of methyl 6-fluoro-5-methoxy-2-methyl-3-indenyl acetate (from Example 5, part E), 9.3 g (0.037 mol) and p-methylsulfonylbenzaldehyde, 6.3 g (1.1 equivalent). The mixture is stirred at reflux under nitrogen for 2 hours. An equal volume of water is added slowly. The solution is heated at reflux (30 minutes), is diluted with water and is extracted with ether, freed of ether by bubbling with nitrogen, and is acidified with 10% hydrochloric acid. The precipitate is collected, is washed thoroughly with water, and is recrystallized from methanol to give (Z)-6-fluoro-5-methoxy-2-methyl-1-(p-methylsulfonylbenzylidene)-2-indenylacetic acid.

33

(B) (Z)-6-Fluoro-5-methoxy-2-methyl-1-(4-methylsulfonylbenzylidene)-3-indenylacetic chloride (Z)-6-fluoro-5-methoxy-2-methyl-1-(p-methylsulfonylbenzylidene)-3-indenylacetic acid (70 mmol) in THF (500 ml) is allowed to react with oxalylchloride (2 M in $CH_2Cl_2$; 70 mmol) under reflux conditions (24 hours). The solvent is evaporated to yield the title compound, which is used as such in the next step.

(C) (Z)-6-Fluoro-5-methoxy-2-methyl-1-(4-methylsulfonylbenzylidene)-1H-3-indenyl-(2-hydroxy) ethane Lithium borohydride (1.38 mmol) in THF (2 ml) is added to the solution of (Z)-5-fluoro-2-methyl-1-(4-methylsulfonylbenzylidene)-3-indenylacetyl chloride (2.78 mmol) in THF (20 ml) at 0° C. The reaction is quenched with HCl (10%, aqueous, 30 ml). After 5 minutes, ethyl acetate (50 ml) is added to extract the product.

The organic extract is washed with water (2×50 ml), is dried over $Na_2SO_4$ and is concentrated. The residue is purified with flash chromatography to yield the title compound (ethylacetate:hexane 8:2) ($R_1$=F, $CH_3O$; $R_2$=$CH_3$; $R_3$=H; $R_4$=H; Y=4-methylsulfonylphenyl, n=2).

EXAMPLE 33

(Z)-5-Fluoro-2-Methyl-1-(3,4,5-Trimethoxybenzylidene)-1H-3-Indenyl-(3-Hydroxy) Propane (A) (Z)-5-Fluoro-2-methyl-1-(3,4,5-trimethoxybenzylidene)-3-indenyl acetic acid 5-fluoro-2-methylindene-3-acetic acid (see Example 1, Part D) is allowed to react with 3,4,5-trimethoxybenzaldehyde according to the procedure of Example 1, part E to obtain (Z)-5-fluoro-2-methyl-1-(3,4,5-trimethoxybenzylidene)-3-indenylacetic acid. $C_{22}H_{21}FO_5$: 384.40; m.p. 168° C.

(B) (Z)-5-Fluoro-2-methyl-1-(3,4,5-trimethoxybenzylidene)-3-indenylacetyl chloride (Z)-5-fluoro-2-methyl-1-(3,4,5-trimethoxybenzylidene)-3-indenylacetic acid (70 mmol) in THF (500 ml) is allowed to react with oxalylchloride (2 M in $CH_2Cl_2$; 35 ml) under reflux conditions (24 hours). The solvent is evaporated to yield the title compound, which is used as such in the next step.

(C) (Z)-5-Fluoro-2-methyl-1-(3,4,5-trimethoxybenzylidene)-3-indenylmethyl-diazomethyl ketone Diazomethane (excess) in ether (700 ml) is allowed to react with the acid chloride (5 g, 12.5 mmol) in $CH_2Cl_2$ (100 ml). After 30 minutes, the solvent is evaporated to give the title compound, which is used in the next step without purification.

(D) (Z)-5-Fluoro-2-methyl-1-(3,4,5-trimethoxybenzylidene)-3-indenylpropionic acid Sodium hydroxide (7 ml, 1M) is added to a solution of silver nitrate (1 g, 5.89 mmol) in water (9 ml). The silver oxide is filtered off and is stirred with a solution of (Z)-5-Fluoro-2-methyl-1-(3,4,5-trimethoxybenzylidene)-3-indenylmethyl-diazomethyl ketone (1 g, 2.44 mmol) in ethanol (100 ml) for 3 hours under reflux conditions. The solution is filtered. The filtrate is treated with base (2N NaOH, 1d), and is acidified with 2N HCl, and is extracted with ethyl acetate. The organic phase is washed with water, is dried over $Na_2SO_4$, and is concentrated. Recrystallization of the residue from acetonitrile gives the title compound.

34

(E) (Z)-5-Fluoro-2-methyl-1-(3,4,5-trimethoxybenzylidene)-3-indenylpropionic acid chloride.

(Z)-5-Fluoro-2-methyl-1-(3,4,5-trimethoxybenzylidene)-3-indenylpropionic acid (2 mmol) in THF (20 ml) is refluxed with oxalylchloride (2M in $CH_2Cl_2$, 2 mmol) for 24 hours. The solvent is evaporated to give the title compound which is used as such in the next step.

(F) (Z)-5-Fluoro-2-methyl-1-(3,4,5-trimethoxybenzylidene)-1H-3-indenyl-(3-hydroxy)propane.

The procedure of Example 32, part C is followed with the acid chloride from part E of this Example to yield the title compound) ($R_1$=F,; $R_2$=$CH_3$; $R_3$=$CH_3$; $R_4$=H; Y=3,4,5-trimethoxyphenyl, p=1).

EXAMPLE 34 rac-(Z)-2-[5-Methoxy-2-Methyl-1-[1-(3,4,5-Trimethoxy Benzylidene) 3-Indenyl]-(1-Hydroxy) Propane (A) 5-Methyl α-(5-methoxy-2-methyl-3-indenyl) propionate A solution of 6-methoxy-2-methyl indanone (13.4 g)(from Example 4B) and methyl α-bromo propionate (21.1 g) in benzene (45 ml) is added over a period of 5 minutes to zinc amalgam (21 g) (prepared according to *Organic Synthesis*, Coll. Vol. 3, p. 444) being stirred in benzene (110 ml) and dry ether (40 ml). A few crystals of iodine are added to start the reaction. The reaction mixture is maintained at reflux temperature (ca. 65° C.). At 3-hour intervals, two batches of zinc amalgam (10 g) and methyl α-bromopropionate (10 g) are added. The mixture is refluxed for 8 hours. After addition of ethanol (30 ml) and acetic acid (150 ml), the mixture is poured into 50% aqueous acetic acid (700 ml). The aqueous layer is extracted twice with ether; the combined organic layers are washed thoroughly with water, ammonium hydroxide and water, dried over sodium sulfate, and are concentrated in vacuo. The residual oil is pumped (at 80° C. bath temperature, 1–2 mm Hg) to give an oil containing methyl α-(1-hydroxy-2-methyl-6-methoxy-3-indanyl)propionate.

A mixture of the above oil, p-toluenesulfonic acid (20 g) monohydrate and anhydrous calcium chloride (20 g) in toluene (250 ml) is heated at reflux overnight and is filtered. The solid residue is washed with toluene. The combined toluene solution is washed with water, saturated aqueous sodium bicarbonate, and water; and is dried over sodium sulfate. After concentration, the residual crude methyl-α-(5-methoxy-2-methyl-3-indenyl)propionate is chromatographed on acid-washed alumina, and the product is eluted with hexanes (1:2).

(B) rac-(Z)-α-[1-(3,4,5-trimethoxybenzylidene)-2-methyl-5-methoxy-3-indenyl]propionic acid A 40% solution of benzyltrimethyl ammonium hydroxide (Triton-B) in methanol (1.63 g) is added to a solution of methyl α-(5-methoxy-2-methyl-3-indenyl)propionate (0.5 g, 1.92 mmol) and 3,4,5-trimethoxybenzaldehyde (0.77 g; 3.9 mmol) in anhydrous pyridine (3 ml). The resulting red-purple solution is stirred at room temperature overnight.

The solution is poured into a mixture of ice and water, is acidified with 2.5N HCl, and is extracted with ether. The ether extract is washed once with 2.5 N HCl and then with water until neutral. The organic phase is dried over $Na_2SO_4$ and concentrated in vacuo to obtain rac-(Z)-α-[1-3,4,5-trimethoxybenzylidene)-2-methyl-5-methoxy-3-indenyl] propionic acid.

(C) rac-(Z)-α-[1-(3,4,5-trimethoxybenzylidene)-2-methyl-5-methoxy-3-indenyl]propionic acid chloride In accordance with the procedure described in Example 33, part E, the product from the preceding step B is used instead of (Z)-5-Fluoro-2-methyl-1-(3,4,5-trimethoxybenzylidene)-3-indenylpropionic acid to yield the title compound, which is used without further purification in the next step.

(D) rac-(Z)-2-[5-Methoxy-2-methyl-1-[1-(3,4,5-trimethoxybenzylidene)-2-methyl-5-methoxy-3-inden-3-yl]-(1-hydroxy)propane rac-(Z)-α-[1-(3,4,5-trimethoxybenzylidene)-2-methyl-5-methoxy-3-indenyl]propionic acid chloride is allowed to react according to the procedure of Example 33, part F to give the title compound) ($R_1$=OCH$_3$,; $R_2$=CH$_3$; $R_3$=CH$_3$; $R_4$=H; Y=3, 4,5-trimethoxyphenyl, p=1 n=1, $R_5$ and $R_6$ form a double bond, $R_7$=H, m=1).

Biological Effects (A) Growth Inhibition

The compounds of Examples #1, #8, and #9 were assayed for their growth inhibitory activity on the human colon carcinoma cell line, SW-480 obtained from ATCC (Rockville, Md.), to ascertain the degree of growth inhibition. Growth inhibition of this cell line is indicative of a benefit on precancerous lesions and neoplasms. The cell line and growth assay employed for such experiments are well characterized, and are used to evaluate the anti-neoplastic properties of compounds. The assay is used by the United States National Cancer Institute in its screening program for new anti-cancer drugs.

Drug stock solutions were made in 100% DMSO and were then diluted with RPMI media for cell culture testing. All drug solutions were prepared fresh on the day of testing. The cultured cells were obtained at passage #99 and grown in RPMI media supplemented with 5% fetal calf serum, and 2 mM glutamine, 100 U/ml penicillin, 100 U/ml streptomycin, and 0.25 µg/ml amphotericin. The cultures were maintained in a humidified atmosphere of 95% air and 5% CO$_2$ at 37° C. The cultures were passaged at preconfluent densities using a solution of 0.05% trypsin and 0.53 mM EDTA. Cells were plated at 1000 cells/well for 96 well flat-bottom microtiter plates.

Tumor cell growth inhibition was assessed using the Sulforhodamine B (SRB) protein binding assay. In this assay, tumor cells were plated in 96-well plates and treated with drug-containing media for six days (continuous 100 mM exposure). For each plate, 6 wells were designated as no treatment controls, six wells as vehicle (0.1% DMSO) controls, and the remaining wells for drug dilutions with three wells per drug. At the end of the exposure period, the cells were fixed and stained with sulforhodamine B, a protein binding dye. The dye was then solubilized, and the optical density of the resulting solution was determined on a 96-well plate reader. The mean dye intensity of the treated wells was then divided by the mean dye intensity in the control wells (6 wells of each) to determine the effect of the drug on the cells. Dye intensity is proportional to the number of cells or amount of protein per well. The resultant "percent inhibition" value then represents the degree of growth inhibition caused by the drug.

Percent growth inhibitions obtained for the compounds of Examples 1, 8 and 9 are shown in Table 1.

TABLE 1

| EXAMPLE | % Growth Inhibition (100 µM) |
|---|---|
| 1 | 71% |
| 8 | 93% |
| 9 | 84% |

In addition, a dose response for growth inhibition was determined for the compound of Example 9, and an IC$_{50}$ value was determined. This value is equivalent to the concentration of drug needed to inhibit tumor cell growth by 50%. IC$_{50}$ value of 29.2 µM was obtained graphically by connecting the mean values for each drug concentration tested. Each experiment included at least three wells per drug concentration. Concentration was plotted on a log scale on the X-axis.

(B) Cyclooxygenase Type I (COX-I) Inhibition

COX-I catalyzes the formation of prostaglandins and thromboxane by the oxidative metabolism of arachidonic acid. The compound of Example 1 of this invention, as well as a positive control, (sulindac sulfide) were evaluated to determine whether they inhibited purified cyclooxygenase Type I (see Table 2 below).

The compounds of this invention were evaluated for inhibitory effects on purified COX-I. The COX-I was purified from ram seminal vesicles, as described by Boopathy, R. and Balasubramanian, J., 239:371–377, 1988. COX-I activity was assayed as described by Evans, A. T., et al., "Actions of Cannabis Constituents on Enzymes Of Arachidonate Metabolism Anti-Inflammatory Potential," Biochem. Pharmacol., 36:2035–2037, 1987. Briefly, purified COX-I was incubated with arachidonic acid (100 µM) for 2.0 min at 37° C. in the presence or absence of test compounds. The assay was terminated by the addition of TCA, and COX-I activity was determined by absorbance at 530 nm.

TABLE 2

| EXAMPLE | COX-I % Inhibition (100 µM) |
|---|---|
| Sulindac sulfide | 86 |
| 1 | 70 |
| 9 | <25 |

(C) Apoptosis

Apoptosis was measured using an assay of cell death based on morphological characteristics of apoptotic cells (i.e., condensed chromatin). Drug preparation and cell culture conditions were the same as for the SRB assay described above, except that HT-29 human colon carcinoma cells were used. Confluent cultures were established in 12.5 cm$^2$ flasks by plating 0.5×10$^6$ cells/flask. The cultures were assayed for apoptosis by fluorescent microscopy following labeling with acridine orange and ethidium bromide. Floating and attached cells were collected by trypsinization and washed three times in PBS. One ml aliquots were centrifuged (3 g). The pellet was resuspended in 25 µl media and 1 µl of a dye mixture containing 100 µg/ml acridine orange and 100 µg/ml ethidium bromide prepared in PBS and mixed gently. Ten µl of the mixture were placed on a microscope slide and covered with a 22 mm$^2$ coverslip, which was examined with 40× dry objectives under epillumination by filter combination.

An observer blinded in regard to the identity of the samples scored at least 100 cells per sample. Apoptotic cells were identified by nuclear condensation of chromatin stained by the acridine orange or ethidium bromide. These results are provided in Table 3 below, along with exisulind as a control.

TABLE 3

Apoptosis Effects of Compounds

| Example | Morphology % Apoptotic Cells 100 μM | DNA Fragmentation FS (100 μM) | $EC_{50}$ (μM) |
|---|---|---|---|
| Exisulind | 48% (@540 μM) | 3.4 (@700 μM) | 425 |
| 1 | | 4.9 | |
| 8 | | 5.4 | 20 |
| 9 | 98% | 6.5 | 89.3 |

Apoptosis was also measured based on the amount of fragmented DNA contained in cell lysates. Briefly, SW-480 colon adenocarcinoma cells were plated in 96-well microtitre plates ("MTP") at a density of 10K cells/well in 180 μl and were incubated for 24 hrs. Cells were then treated with 20 μl aliquots of appropriately diluted compound, and allowed to incubate for an additional 48 hrs.

After the incubation, samples were prepared according to the following steps. The MTP was centrifuged (15 min., 1000 rpm) and the supernatant was carefully removed by fast inversion of the MTP. The cell pellets in each well were resuspended in 200 μl lysis buffer and incubated for 45 min. at room temperature to lyse the cells. The lysates were then centrifuged (15 min., 1000 rpm) and 20 μl aliquots of the supernatant (=cytoplasmic fraction) were transferred into the streptavidin-coated MTP for analysis. Care was taken not to shake the lysed pellets in the MTP (=cell nucleii containing high molecular weight, unfragmented DNA). Samples were analyzed immediately, because storage at 4° C. or −20° C. reduces the ELISA-signals.

Samples were then processed according to a DNA fragmentation assay protocol, and dose-response curves were generated based on optical density readings. Quantification of DNA was done by a commercially available photometric enzyme-immunoassay manufactured by Mannheim-Boehringer under the name "Cell Death Detection ELISA $^{plus}$". The assay is based on a quantitative sandwich-enzyme-immunoassay-principle using mouse monoclonal antibodies directed against DNA and histones, respectively. This allows the specific determination of mono and oligonucleosomes in the cytoplasmatic fraction of cell lysates. In brief, the assay procedure is as follows. The sample (cell-lysate, serum, culture-supematant etc.) is placed into a streptavidin-coated MTP. Subsequently, a mixture of anti-histone-biotin and anti-DNA-POD is followed by incubation for 2 hours. During the incubation period, the anti-histone antibody binds to the histone-component of the nucleosomes and simultaneously fixes the immunocomplex to the streptavidin-coated MTP via its biotinylation. Additionally, the anti-DNA-POD antibody reacts with the DNA component of the nucleosomes. After removal of unbound antibodies by washing, the amount of nucleosomes is quantified by the POD retained in the immunocomplex. POD is determined photometrically with ABTS® (2,2'-Azino-di[3-ethylbenzthiazolin-sulfonate]) as substrate.

Fold stimulation (FS=ODmax/ODveh), an indicator of apoptotic response, was determined for each compound tested. $EC_{50}$ values were determined either specifically by data analysis software, or by estimates based on the effective concentration range of each compound (ECR=min. effective dose-min. dose to peak effect). These FS and $EC_{50}$ values for the tested compounds are listed above in Table 3.

In addition, using the DNA fragmentation test above, dose responses for the compounds of Example 8 and 9 were obtained. Those data are set forth in Tables 4 and 5, respectively.

TABLE 4

Data For Example 8

| Dose [μM] | Apoptosis Level (Mean OD Value ± SD) | Growth (% Vehicle) |
|---|---|---|
| 0 | 0.249 ± 0.05 | 100 ± 6.4 |
| 0.001 | 0.252 ± 0.017 | 101 ± 4.6 |
| 0.01 | 0.272 ± 0.013 | 109 ± 9.2 |
| 0.1 | 0.277 ± 0.044 | 105 ± 5.5 |
| 1 | 0.304 ± 0.044 | 103 ± 6.6 |
| 10 | 0.355 ± 0.049 | 24 ± 16 |
| 100 | 0.974 ± 0.124 | 5 ± 0.6 |
| 500 | 0.76 ± 0.113 | 9 ± 3.4 |

TABLE 5

Data For Example 9

| Dose [μM] | Apoptosis Level (Mean OD Value ± SD) | Growth (% Vehicle) |
|---|---|---|
| 0 | 0.346 ± 0.032 | 100 ± 5.2 |
| 0.01 | 0.272 ± 0.033 | 107 ± 7.4 |
| 0.05 | 0.285 ± 0.03 | 108 ± 9.6 |
| 0.1 | 0.312 ± 0.05 | 111 ± 16.7 |
| 0.5 | 0.258 ± 0.03 | 114 ± 18.1 |
| 1 | 0.296 ± 0.052 | 106 ± 6.3 |
| 5 | 0.239 ± 0.024 | 100 ± 8.3 |
| 10 | 0.261 ± 0.022 | 103 ± 9.3 |
| 50 | 0.259 ± 0.068 | 35 ± 0.246 |
| 100 | 0.742 ± 0.095 | 21 ± 0.65 |

Based on the data obtained from the DNA fragmentation tests in Tables 4 and 5, fold stimulations values for those compounds are also calculated at 100 μM by dividing the optical densities obtained at 100 μM by the optical densities of the control. Based on the data in Tables 4 and 5, fold stimulation values of 3.9 and 2.1 for the compounds of Examples 8 and 9 are obtained, accordingly.

The compounds of this invention can be formulated with pharmaceutically acceptable carriers into unit dosage forms in a conventional manner so that the patient in need of therapy for precancerous lesions can periodically (e.g., once or more per day) take a compound according to the methods of this invention. The exact initial dose of the compounds of this invention can be determined with reasonable experimentation. One skilled in the art should understand that the initial dosage should be sufficient to achieve a blood plasma concentration approaching a percentage of the $IC_{50}$ value of the compound, with the percentage depending on the chemopreventative or chemotherapeutic indication. The initial dosage calculation would also take into consideration several factors, such as the formulation and mode of administration, e.g. oral or intravenous, of the particular compound. For example, assuming a patient with an average circulatory system volume of about four liters, based on the $IC_{50}$ values for compounds of this invention, one would calculate a dosage of about 42–84 mg of such compound for intravenous administration to achieve a systemic circulatory concentration equivalent to the $IC_{50}$ concentration above.

It will be understood that various changes and modifications can be made in the details of procedure, formulation and use without departing from the spirit of the invention, especially as defined in the following claims.

We claim:

1. A method for inhibiting the growth of neoplastic cells comprising exposing the cells to a growth inhibiting effective amount a compound of Formula I:

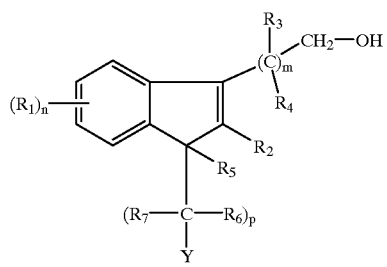

wherein $R_1$ is independently selected in each instance from the group consisting of hydrogen, halogen, lower alkoxy, hydroxy, lower alkyl, lower alkyl mercapto, lower alkylsulfonyl, lower alkylamino, di-lower alkyl amino, amino, nitro, nitrile, lower alkyl carboxylate, $CO_2H$, and sulfonamido;

$R_2$ is selected from the group consisting of hydrogen and lower alkyl;

$R_3$ and $R_4$ are independently selected from the group consisting of hydrogen, hydroxy, amino, lower alkyl amino, alkylamino alkyl, lower alkyl, lower alkoxy, hydroxyalkyl, lower alkylmercapto, and lower alkylsulfonyl;

$R_5$ is selected from the group consisting of hydrogen and hydroxy, or $R_5$ and $R_6$ together form a double bond;

$R_6$ is selected from the group consisting of hydrogen and hydroxy, or $R_6$ and $R_7$ together form an oxygen when $R_5$ and $R_6$ together do not form a double bond;

$R_7$ is selected from the group consisting of hydrogen, amino, lower alkyl amino, di-lower alkylamino;

m is an integer from 0 to 3;

n is an integer from 0 to 4;

p is an integer from 1 to 3;

Y is selected from the group consisting of phenyl, quinolinyl, isoquinolinyl, pyridinyl, pyrimidinyl, pyrazinyl, imidazolyl, indolyl, benzimidazolyl, triazinyl, tetrazolyl, thiophenyl, furanyl, thiazolyl, pyrazolyl, or pyrrolyl, or subsituted variants thereof wherein the substituents are one to three independently selected from the group consisting of halogen, lower alkyl, lower alkoxy, amino, lower alkylamino, di-lower alkylamino, hydroxy, nitro, nitrile, $-CO_2H$, $-SO_2NH_2$, lower alkyl mercapto, and lower alkyl sulfonyl; and pharmaceutically acceptable salts thereof.

2. A method for regulating apoptosis in human cells comprising exposing the cells to an effective amount a compound of Formula I:

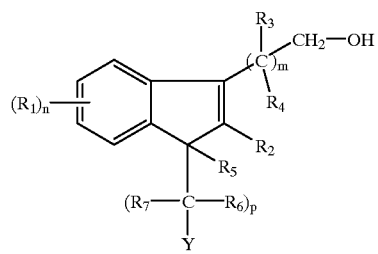

wherein $R_1$ is independently selected in each instance from the group consisting of hydrogen, halogen, lower alkoxy, hydroxy, lower alkyl, lower alkyl mercapto, lower alkylsulfonyl, lower alkylamino, di-lower alkyl amino, amino, nitro, nitrile, lower alkyl carboxylate, $CO_2H$, and sulfonamido;

$R_2$ is selected from the group consisting of hydrogen and lower alkyl;

$R_3$ and $R_4$ are independently selected from the group consisting of hydrogen, hydroxy, amino, lower alkyl amino, alkylamino alkyl, lower alkyl, lower alkoxy, hydroxyalkyl, lower alkylmercapto, and lower alkylsulfonyl;

$R_5$ is selected from the group consisting of hydrogen and hydroxy, or $R_5$ and $R_6$ together form a double bond;

$R_6$ is selected from the group consisting of hydrogen and hydroxy, or $R_6$ and $R_7$ together form an oxygen when $R_5$ and $R_6$ together do not form a double bond;

$R_7$ is selected from the group consisting of hydrogen, amino, lower alkyl amino, di-lower alkylamino;

m is an integer from 0 to 3;

n is an integer from 0 to 4;

p is an integer from 1 to 3;

Y is selected from the group consisting of phenyl, quinolinyl, isoquinolinyl, pyridinyl, pyrimidinyl, pyrazinyl, imidazolyl, indolyl, benzimidazolyl, triazinyl, tetrazolyl, thiophenyl, furanyl, thiazolyl, pyrazolyl, or pyrrolyl, or subsituted variants thereof wherein the substituents are one to three independently selected from the group consisting of halogen, lower alkyl, lower alkoxy, amino, lower alkylamino, di-lower alkylamino, hydroxy, nitro, nitrile, $-CO_2H$, $-SO_2NH_2$, lower alkyl mercapto, and lower alkyl sulfonyl; and pharmaceutically acceptable salts thereof.

3. The method of claim 1 wherein $R_1$ is selected from the group consisting of halogen, lower alkoxy, lower alkylsulfonyl, lower alkyl amino, di-lower alkyl amino, amino, lower alkylcarboxylate, $-CO_2H$, and sulfonamido.

4. The method of claim 3 wherein $R_1$ is selected from the group consisting of halogen, lower alkoxy, lower alkylsulfonyl, lower alkyl amino, di-lower alkyl amino, and amino.

5. The method of claim 4 wherein $R_1$ is halogen.

6. The method of claim 1 wherein $R_2$ is lower alkyl.

7. The method of claim 4 wherein $R_2$ is lower alkyl.

8. The method of claim 1 wherein $R_3$ and $R_4$ are independently selected from the group consisting of hydrogen, hydroxy, amino, lower alkylamino, alkylaminoalkyl and lower alkylsulfonyl.

9. The method of claim 7 wherein $R_3$ and $R_4$ are independently selected from the group consisting of hydrogen, hydroxy, amino, lower alkylamino, alkylaminoalkyl and lower alkylsulfonyl.

10. The method of claim 1 wherein $R_3$ and $R_4$ are independently selected from the group consisting of hydrogen, hydroxy, and amino.

11. The method of claim 4 wherein $R_3$ and $R_4$ are independently selected from the group consisting of hydrogen, hydroxy, and amino.

12. The method of claim 8 wherein $R_3$ and $R_4$ are the same.

13. The method of claim 11 wherein $R_3$ and $R_4$ are the same.

14. The method of claim 13 wherein $R_3$ and $R_4$ are both hydrogen.

15. The method of claim 1 wherein $R_6$ is hydrogen, or $R_5$ and $R_6$ together form a double bond.

16. The method of claim 11 wherein $R_6$ is hydrogen, or $R_5$ and $R_6$ together form a double bond.

17. The method of claim 1 wherein Y is selected from the group consisting of phenyl, quinolinyl, isoquinolinyl, pyridinyl, pyrimidinyl, pyrazinyl, imidazolyl, indolyl, benzimidazolyl, triazinyl, or tetrazolyl, or said substituted variants therof.

18. The method of claim 16 wherein Y is selected from the group consisting of phenyl, quinolinyl, isoquinolinyl, pyridinyl, pyrimidinyl, pyrazinyl, imidazolyl, indolyl, benzimidazolyl, triazinyl, or tetrazolyl, or said substituted variants therof.

19. The method of claim 18 wherein the substituents on the Y-ring are independently selected from the group consisting of halogen, lower alkoxy, di-loweralkylamino, amino or hydroxy.

20. The method of claim 19 wherein the substituents on the Y-ring are independently selected from the group consisting of halogen, lower alkoxy, and di-loweralkylamino.

21. The method of claim 20 wherein m, n and p are each 1.

22. The method of claim 2 wherein $R_1$ is selected from the group consisting of halogen, lower alkoxy, lower alkylsulfonyl, lower alkyl amino, di-lower alkyl amino, amino, lower alkylcarboxylate, —$CO_2H$, and sulfonamido.

23. The method of claim 22 wherein $R_1$ is selected from the group consisting of halogen, lower alkoxy, lower alkylsulfonyl, lower alkyl amino, di-lower alkyl amino, and amino.

24. The method of claim 23 wherein $R_1$ is halogen.

25. The method of claim 2 wherein $R_2$ is lower alkyl.

26. The method of claim 24 wherein $R_2$ is lower alkyl.

27. The method of claim 2 wherein $R_3$ and $R_4$ are independently selected from the group consisting of hydrogen, hydroxy, amino, lower alkylamino, alkylaminoalkyl and lower alkylsulfonyl.

28. The method of claim 26 wherein $R_3$ and $R_4$ are independently selected from the group consisting of hydrogen, hydroxy, amino, lower alkylamino, alkylaminoalkyl and lower alkylsulfonyl.

29. The method of claim 2 wherein $R_3$ and $R_4$ are independently selected from the group consisting of hydrogen, hydroxy, and amino.

30. The method of claim 23 wherein $R_3$ and $R_4$ are independently selected from the group consisting of hydrogen, hydroxy, and amino.

31. The method of claim 27 wherein $R_3$ and $R_4$ are the same.

32. The method of claim 30 wherein $R_3$ and $R_4$ are the same.

33. The method of claim 32 wherein $R_3$ and $R_4$ are both hydrogen.

34. The method of claim 2 wherein $R_6$ is hydrogen, or $R_5$ and $R_6$ together form a double bond.

35. The method of claim 30 wherein $R_6$ is hydrogen, or $R_5$ and $R_6$ together form a double bond.

36. The method of claim 2 wherein Y is selected from the group consisting of phenyl, quinolinyl, isoquinolinyl, pyridinyl, pyrimidinyl, pyrazinyl, imidazolyl, indolyl, benzimidazolyl, triazinyl, or tetrazolyl, or said substituted variants therof.

37. The method of claim 25 wherein Y is selected from the group consisting of phenyl, quinolinyl, isoquinolinyl, pyridinyl, pyrimidinyl, pyrazinyl, imidazolyl, indolyl, benzimidazolyl, triazinyl, or tetrazolyl, or said substituted variants therof.

38. The method of claim 27 wherein the substituents on the Y-ring are independently selected from the group consisting of halogen, lower alkoxy, di-loweralkylamino, amino or hydroxy.

39. The method of claim 28 wherein the substituents on the Y-ring are independently selected from the group consisting of halogen, lower alkoxy, and di-loweralkylamino.

40. The method of claim 29 wherein m, n and p are each 1.

41. A method of treating a patient having neoplasia comprising administering a pharmacologically effective amount of a compound of Formula I to the patient with a neoplasia sensitive to such a compound:

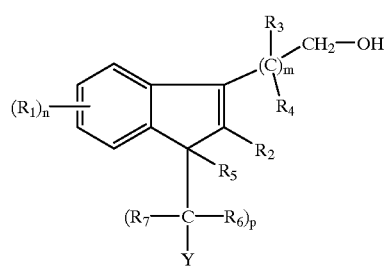

wherein
  $R_1$ is independently selected in each instance from the group consisting of hydrogen, halogen, lower alkoxy, hydroxy, lower alkyl, lower alkyl mercapto, lower alkylsulfonyl, lower alkylamino, di-lower alkyl amino, amino, nitro, nitrile, lower alkyl carboxylate, $CO_2H$, and sulfonamido;
  $R_2$ is selected from the group consisting of hydrogen and lower alkyl;
  $R_3$ and $R_4$ are independently selected from the group consisting of hydrogen, hydroxy, amino, lower alkyl amino, alkylamino alkyl, lower alkyl, lower alkoxy, hydroxyalkyl, lower alkylmercapto, and lower alkylsulfonyl;
  $R_5$ is selected from the group consisting of hydrogen and hydroxyl or $R_5$ and $R_6$ together form a double bond;
  $R_6$ is selected from the group consisting of hydrogen and hydroxy, or $R_6$ and $R_7$ together form an oxygen when $R_5$ and $R_6$ together do not form a double bond;
  $R_7$ is selected from the group consisting of hydrogen, amino, lower alkyl amino, di-lower alkylamino;
  m is an integer from 0 to 3;
  n is an integer from 0 to 4;
  p is an integer from 1 to 3;
  Y is selected from the group consisting of phenyl, quinolinyl, isoquinolinyl, pyridinyl, pyrimidinyl, pyrazinyl, imidazolyl, indolyl, benzimidazolyl, triazinyl, tetrazolyl, thiophenyl, furanyl, thiazolyl, pyrazolyl, or pyrrolyl, or subsituted variants thereof wherein the substituents are one to three independently selected from the group consisting of halogen, lower alkyl, lower alkoxy, amino, lower alkylamino, di-lower alkylamino, hydroxy, nitro, nitrile, $CO_2H$, $-SO_2NH_2$, lower alkyl mercapto, and lower alkyl sulfonyl; and pharmaceutically acceptable salts thereof.

42. The method of claim 41 wherein $R_1$ is selected from the group consisting of halogen, lower alkoxy, lower alkylsulfonyl, lower alkyl amino, di-lower alkyl amino, amino, lower alkylcarboxylate, $-CO_2H$, and sulfonamido.

43. The method of claim 42 wherein $R_1$ is selected from the group consisting of halogen, lower alkoxy, lower alkylsulfonyl, lower alkyl amino, di-lower alkyl amino, and amino.

44. The method of claim 43 wherein $R_1$ is halogen.

45. The method of claim 44 wherein $R_2$ is lower alkyl.

46. The method of claim 45 wherein $R_3$ and $R_4$ are independently selected from the group consisting of hydrogen, hydroxy, amino, lower alkylamino, alkylaminoalkyl and lower alkylsulfonyl.

47. The method of claim 46 wherein $R_3$ and $R_4$ are independently selected from the group consisting of hydrogen, hydroxy, and amino.

48. The method of claim 47 wherein $R_3$ and $R_4$ are the same.

49. The method of claim 48 wherein $R_3$ and $R_4$ are both hydrogen.

50. The method of claim 49 wherein $R_6$ is hydrogen, or $R_5$ and $R_6$ together form a double bond.

51. The method of claim 50 wherein Y is selected from the group consisting of phenyl, quinolinyl, isoquinolinyl, pyridinyl, pyrimidinyl, pyrazinyl, imidazolyl, indolyl, benzimidazolyl, triazinyl, or tetrazolyl, or said substituted variants therof.

52. The method of claim 51 wherein the substituents on the Y-ring are independently selected from the group consisting of halogen, lower alkoxy, di-loweralkylamino, amino or hydroxy.

* * * * *